United States Patent
Wagner et al.

(10) Patent No.: US 9,956,226 B2
(45) Date of Patent: May 1, 2018

(54) METHODS AND COMPOUNDS FOR THE INHIBITION OF CELLULAR PROLIFERATION

(71) Applicant: President and Fellows of Harvard College, Cambridge, MA (US)

(72) Inventors: Gerhard Wagner, Chestnut Hill, MA (US); Ricard A. Rodriguez-Mias, Seattle, WA (US); Patrick R. Hagner, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days. days.

(21) Appl. No.: 14/767,102

(22) PCT Filed: Feb. 11, 2014

(86) PCT No.: PCT/US2014/015679
§ 371 (c)(1),
(2) Date: Aug. 11, 2015

(87) PCT Pub. No.: WO2014/124412
PCT Pub. Date: Aug. 14, 2014

(65) Prior Publication Data
US 2015/0374707 A1    Dec. 31, 2015

Related U.S. Application Data

(60) Provisional application No. 61/763,017, filed on Feb. 11, 2013.

(51) Int. Cl.
*A61K 31/5365*    (2006.01)
*A61K 31/343*    (2006.01)
*A61K 31/36*    (2006.01)
*A61K 31/357*    (2006.01)

(52) U.S. Cl.
CPC ........ *A61K 31/5365* (2013.01); *A61K 31/343* (2013.01); *A61K 31/357* (2013.01); *A61K 31/36* (2013.01)

(58) Field of Classification Search
CPC .. A61K 31/343; A61K 31/36; A61K 31/5365; A61K 31/357
See application file for complete search history.

(56) References Cited

U.S. PATENT DOCUMENTS 4,999,369 A    3/1991    Bair
2004/0010001 A1    1/2004    Au et al.
2006/0281719 A1    12/2006    Lloyd Potter et al.

OTHER PUBLICATIONS

Chung et al (Chemico-Biological Interactions 193 (2011) 43-49).*
International Search Report issued from corresponding PCT/US2014/015679, dated Jul. 11, 2014.
Rhee et al. Synthesis, Cytotoxicity and Topoisomerase II Inhibitory Activity of Benzonaphtho-furandiones. Bull. Korean Chem. Soc. 32(7): 2391-2396, 2011.

* cited by examiner

*Primary Examiner* — Angela C Brown-Pettigrew
(74) *Attorney, Agent, or Firm* — Banner & Witcoff, Ltd.

(57) ABSTRACT

Methods for inhibiting translation, treating a cellular proliferative disorder, and inhibiting proliferation of cells using the compounds disclosed herein are provided.

3 Claims, 12 Drawing Sheets

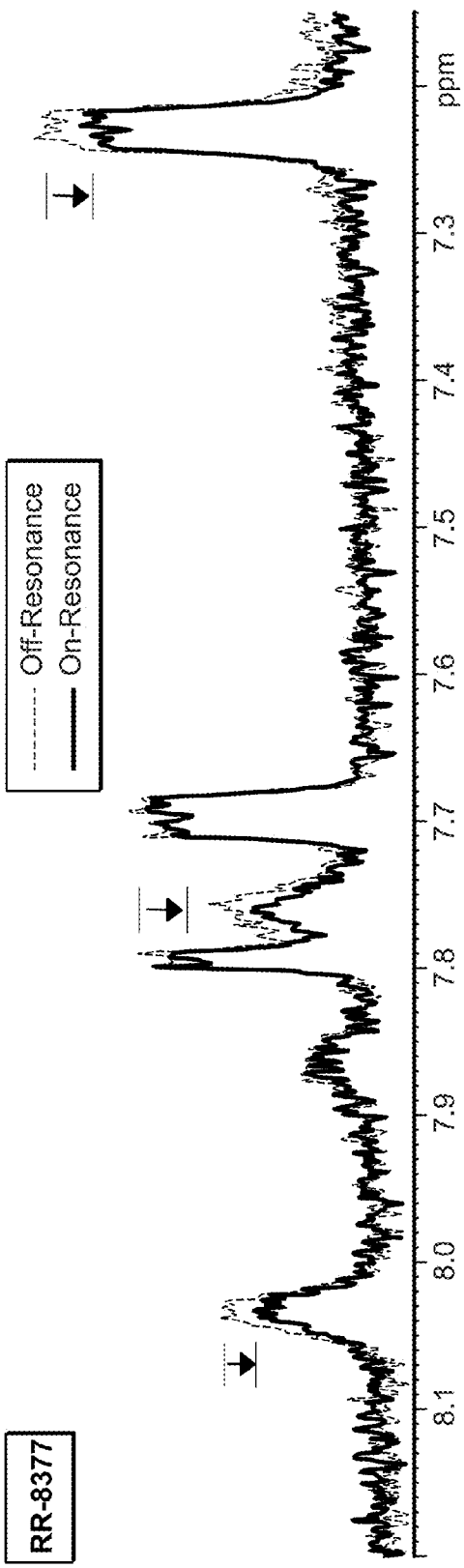

METHODS AND COMPOUNDS FOR THE INHIBITION OF CELLULAR PROLIFERATION

RELATED APPLICATION DATA

This application claims priority to U.S. Provisional Patent Application No. 61/763,017 filed on Feb. 11, 2013 and is hereby incorporated herein by reference in its entirety for all purposes.

STATEMENT OF GOVERNMENT INTERESTS

This invention was made with Government support under Grant Number NIH P01-GM047467 and R01-CA068262, NIH/NHBLI T32-HL07623-25, NIH K01-DK05198 and NIH R01 AI090671. The Government has certain rights in the invention.

FIELD

The present invention relates to compounds, which inhibit translation initiation, pharmaceutical compositions of the compounds, and methods of treating medical disorders.

BACKGROUND

The regulation of protein synthesis at the level of translation initiation plays a key role in the control of cell growth, proliferation, and apoptosis. Translation, the mRNA-directed synthesis of proteins, occurs in three distinct steps: initiation, elongation and termination. Translation initiation is a complex process in which the two ribosomal subunits and methionyl tRNA (met-tRNAi) assemble on a properly aligned mRNA to commence chain elongation at the AUG initiation codon. The interaction between the initiation factors eIF4E and eIF4G is a major component of this process. eIF4E binds the 7-methylguanosine cap structure found at the 5' ends of most messenger RNAs. Its binding partner eIF4G, a scaffold protein, provides a docking site for other initiation factors, including the RNA helicase eIF4A. Collectively, eIF4E, eIF4G, and eIF4A form a ternary complex referred to as eIF4F. Once assembled, this complex recruits the 40S ribosomal subunit to the 5' end of the mRNA molecule as a result of the interaction of eIF3 with eIF4G, followed by scanning of the 40S subunit to the initiation codon where it joins with the 60S subunit. This process is facilitated by eIF4A, with the requirement for its helicase activity being directly proportional to the amount of secondary structure in the 5' UTR that must be melted for scanning to occur.

Translation initiation is a critical step in the regulation of cell growth because the expression of most oncogenes and cell growth regulatory proteins is translationally regulated. Biosynthesis of many growth-promoting proteins is suppressed on the translation-initiation level, and several forms of cancer exhibit an out-of-balance translation initiation machinery. Although inhibitors of translation exist, most, if not all, act nonspecifically on all translation.

Many types of tumor cells are characterized by aberrant protein translation initiation mechanisms, e.g., association or binding of certain translation initiation factors. For example, the interaction of the cap-binding protein eIF4E with the mRNA cap, the scaffold protein eIF4G, and the regulatory 4E-BPs, are involved in cell transformation. Small-molecule inhibitors of the eIF4E/eIF4G interaction have been identified and found to possess anti-tumor activity.

Recruitment of the capped 5' end of an mRNA to the small ribosomal subunit is thought to be the major rate-limiting step in eukaryotic translation initiation. This process is tightly regulated and requires the stepwise assembly of a large multiprotein complex centered on the trimeric complex eIF4F, comprised of the translation initiation factors eIF4E, eIF4G, and eIF4A. Cap-bound eIF4F recruits the 40S ribosomal subunit through the interaction of eIF3 with eIF4G, which initiates scanning to the initiation codon where it joins with the 60S subunit. This process is facilitated by eIF4A, with the requirement for its helicase activity directly proportional to the amount of secondary structure in the 5' UTR that must be melted for scanning to occur. All eIF4G proteins bind eIF4E through a motif of sequence Y(X)4LΦ, where X is variable and Φ is hydrophobic. This motif forms a helical peptide structure, which binds a conserved surface of hydrophobic residues on the dorsal side of eIF4E.

Cellular mRNAs differ greatly in their requirement for eIF4F for efficient translation and in the composition of the 5' UTR. The majority of growth and proliferation related proteins are encoded by "weak" mRNAs containing long highly structured 5' UTRs which have lower translational efficiency than "strong" mRNAs, which contain relatively short and unstructured 5' UTRs. Translation of weak mRNAs is highly eIF4F dependent and is preferentially enhanced when the level of eIF4F complex is increased by eIF4E overexpression. The amount of eIF4E available for complex formation is controlled by a class of small proteins termed 4E-BPs which contain the Y(X)4LΦ motif and bind to the same surface as eIF4G. In response to stimuli such as nutrients and growth factors 4E-BPs undergo a set of hierarchical phosphorylation events. Hyperphosphorylated forms of 4E-BPs bind eIF4E much more weakly than hypophosphorylated forms, and thus 4E-BP phosphorylation acts as a switch to up-regulate the level of eIF4F and cap-dependent translation.

Misregulation of cap-dependent translation due to overexpression of eIF4E and the other components of the eIF4F complex is thought to play an important role in the development of many forms of cancer. In cultured mammalian cells overexpression of eIF4E or eIF4G induces malignant transformation while overexpression of 4E-BP1 partially reverses transformation by eIF4E. In addition, etopic expression of nonphosphorylatable forms of 4E-BP1 can inhibit proliferation and/or induce apoptosis in cancer cell lines. Inhibition of the eIF4F complex is useful for cancer therapy. See PCT/US2006/002093 hereby incorporated by reference in its entirety.

The disruption of proper translational regulation by elevated levels of eIF4F complexes is an important factor in carcinogenesis. A wide variety of tumors have been found to have abnormally elevated eIF4E levels, and eIF4G is amplified in some lung cancers. The overexpression of eIF4E in cultured cells can cause them to exhibit a malignant transformed phenotype: rapid proliferation, loss of contact inhibition, and anchorage-independent growth. This transformation is dependent on eIF4E's ability to bind eIF4G, as co-expression of 4E-BP1 in these cells can partially reverse their malignant properties. Elevated eIF4E levels are detected in cancers of the breast, head, neck, bladder, colon, prostate, gastrointestinal tract and lung, Hodgkin's lymphomas, and neuroblastomas. In breast cancer patients, the risk of cancer recurrence and cancer-related death is correlated with the level of eIF4E overexpression. The other components of eIF4F are overexpressed in specific types of cancer: eIF4G in squamous cell lung carcinomas, and eIF4A in melanomas and primary hepatocellular carcinomas.

Loss of proper regulation of the eIF4E-eIF4G interaction plays an important role in the development of many cancers. The protein-protein interaction between eIF4E and eIF4G is an essential step in cap-dependent translation initiation. Because the translation of the mRNAs encoding most proteins involved in cellular growth and proliferation is highly cap-dependent, regulation of the level of complex formation between eIF4E and eIF4G plays an important role in the control of these processes. The interaction between these proteins is inhibited by the 4E binding proteins (4E-BPs), which compete with eIF4G for binding to the same surface on eIF4E. Phosphorylation of specific sites on 4E-BPs in response to growth and proliferation signals inhibits their ability to bind eIF4E.

The level of eIF4E/eIF4G complex formation also plays a role in the control of apoptosis. 4E-BP1 has been found to undergo a caspase cleavage of its C-terminus, which removes a motif necessary for it to undergo phosphorylation, leading to increased 4E-BP binding to eIF4E and inhibition of cap-dependent translation. This inhibition causes a shift in the levels of pro and anti apopoptic proteins to favor apoptosis. Experiments in cultured cells have shown that peptides containing the eIF4E recognition motif of eIF4G fused to a penetrating sequence can induce apoptosis.

In general, translation initiation is beneficial for inhibiting cellular proliferative disorders, whether cancerous or non-cancerous and translation initiation is an accepted target for cancer treatments. See Funda Meric and Kelly Hunt, Translation Initiation in Cancer: A Novel Target for Therapy, Molecular Cancer Therapeutics, Vol. 1, 971-979, September 2002; S. J. Watkins and C. J. Norbury, Translation Initiation and Its Deregulation During Tumorigenesis, British Journal of Cancer (2002) 86, 1023-1027; Igor Rosenwald, The Role of Translation in Neoplastic Transformation from a Pathologist's Point of View, Oncogene (2004) 23, 3230-3247; Igor Rosenwald, Songtao Wang, Lou Savas, Bruce Woda, James Pullman, Expression of Translation Initiation Factor eIF-2α is Increased in Benign and Malignant Melanocytic and Colonic Epithelial Neoplasms, Cancer, Vol. 98, No. 5, (2003); Songtao Wang, Igor Rosenwald, Michael Hutzler, German Pihan, Lou Savas, Jane-Jane Chen and Bruce Woda, Expression of the Eukaryotic Translation Initiation Factors 4E and 2α in Non-Hodgkin's Lymphomas, American Journal of Pathology, Vol. 155, 247-255 (1999); B. Bilanges and D. Stokoe, Mechanisms of Translational Deregulation in Human Tumors and Therapeutic Intervention Strategies, Oncogene (2007) 26, 5973-5990; Songtao Wang, Ricardo Lloyd, Michael Hutzler, Igor Rosenwald, Marjorie Safran, Nilima Patwardhan and Ashraf Khan, Expression of Eukaryotic Translation Initiation Factors 4E and 2α Correlates with the Progression of Thyroid Carcinoma, Thyroid, Vol. 11, No. 12 1101-1107 (2001).

SUMMARY

Embodiments of the present invention are directed to compounds and methods that inhibit translation initiation. Embodiments of the present invention are directed to compounds and methods that inhibit translation initiation and selectively suppress synthesis of growth factors and oncogene products. In particular, embodiments of the present invention are directed to compounds and methods of inhibiting the protein-protein interaction between eukaryotic translation initiation factors eIF4E and eIF4G. Such compounds and methods are useful for treating (1) proliferative disorders, (2) non-proliferative, degenerative disorders, (3) viral infections, (4) disorders associated with viral infections and/or (5) non-proliferative metabolic disorders such as type II diabetes where inhibition of translation initiation is beneficial.

In at least certain examples, the compounds of the present invention are effective to inhibit translation. In certain examples, the compounds of the present invention are effective to inhibit cellular proliferation. In another example, the compounds of the present invention are effective to inhibit viral infections. In another example, the compounds of the present invention are effective to treat or relieve symptoms associated with proliferative disorders, non-proliferative, degenerative disorders, viral infections, and/or non-proliferative metabolic disorders.

Some of the compounds described herein may contain one or more centers of asymmetry and may give rise to diastereoisomers and optical isomers. The present invention is meant to include such diastereoisomers as well as their racemic and resolved, optically active forms. Optically active (R) and (S) isomers may be resolved using conventional techniques. Some of the compounds described herein may contain olefinic double bonds, and unless otherwise specified, are meant to include both E and Z geometric isomers.

In accordance with a method aspect, a method of treating a cellular proliferative disorder by providing and/or administering a compound described herein to a mammal, e.g., a human or a non-human (e.g., a non-human primate), is provided. In one example, the cellular proliferative disorder is cancer. In accordance with other examples, a method of treating a non-proliferative, degenerative disorder by providing and/or administering a compound described herein to a mammal, e.g. a human or a non-human mammal, is provided. In accordance with other examples, a method of treating a viral infection by providing and/or administering a compound described herein to a mammal, e.g. a human or a non-human mammal, is provided. In accordance with other examples, a method of treating a disorder associated with a viral infection by providing and/or administering a compound described herein to a mammal, e.g. a human or a non-human mammal, is provided.

In accordance with an additional aspect, kits are provided for the treatment of (1) proliferative disorders, (2) non-proliferative, degenerative disorders, (3) viral infections, (4) disorders associated with viral infections, and/or (5) non-proliferative metabolic disorders such as type II diabetes where inhibition of translation initiation is beneficial. In one aspect, the kits comprise a compound described herein, a pharmaceutically acceptable carrier, and optionally, instructions for use. The pharmaceutical composition can be administered to a human subject or a non-human subject depending on the disorder to be treated.

It will be recognized by the person of ordinary skill in the art that the compounds, compositions, methods and kits disclosed herein provide significant advantages over prior technology. Compounds, compositions, methods and kits can be designed or selected to relieve and/or alleviate symptoms in a patient suffering from one or more disorders. These and other aspects and examples are described below.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 5A depicts resonances from aromatic protons of RR-8377 in the presence of 25 fold excess eIF4E.

Figure 1A:
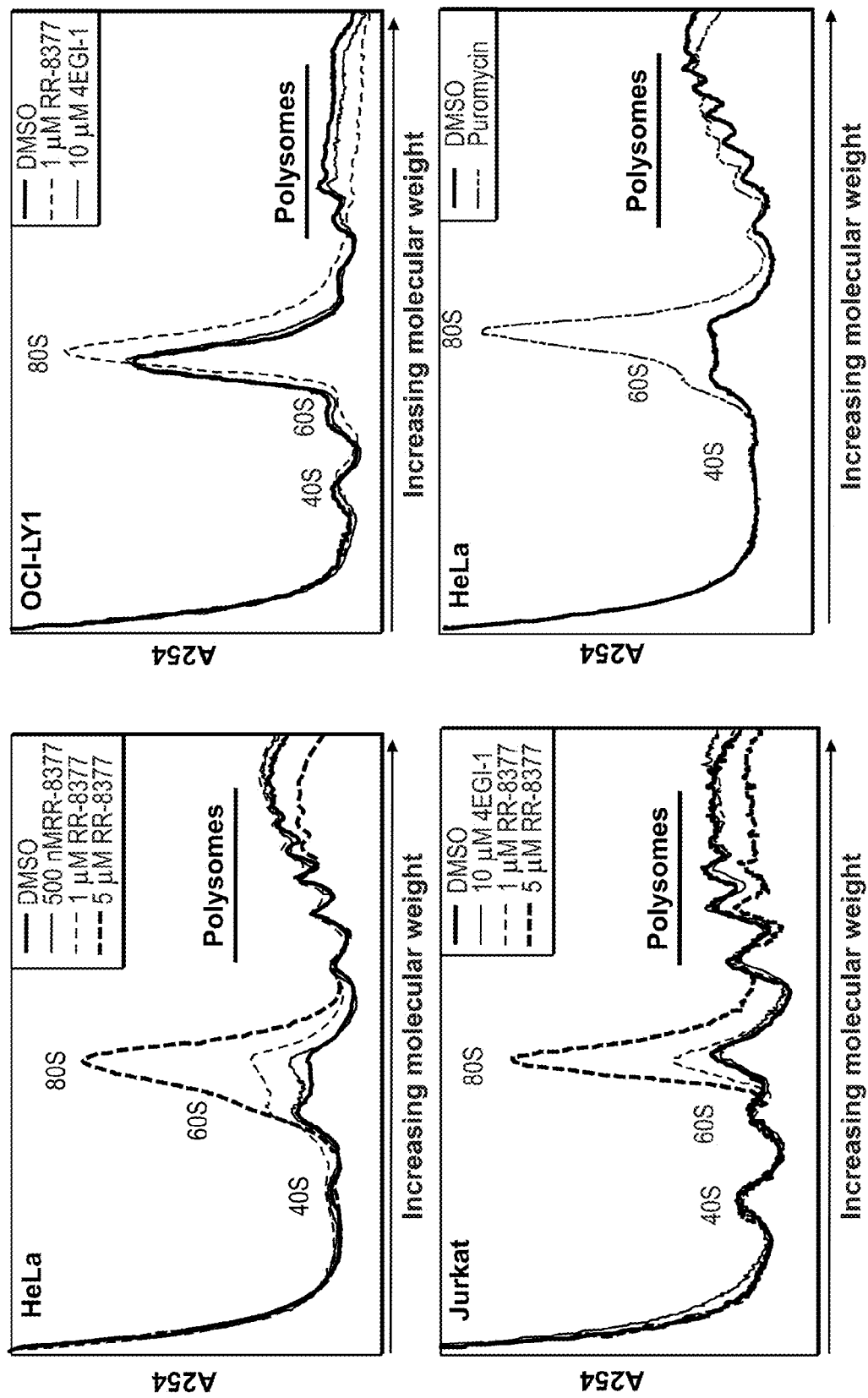
FIG. 1A depicts graphical data of cytoplasmic lysates from HeLa, Jurkat or OCI-LY1 cells treated with multiple doses of RR-8377, 4EGI-1 (four hours) and puromycin (thirty minutes).
Figure 1B:
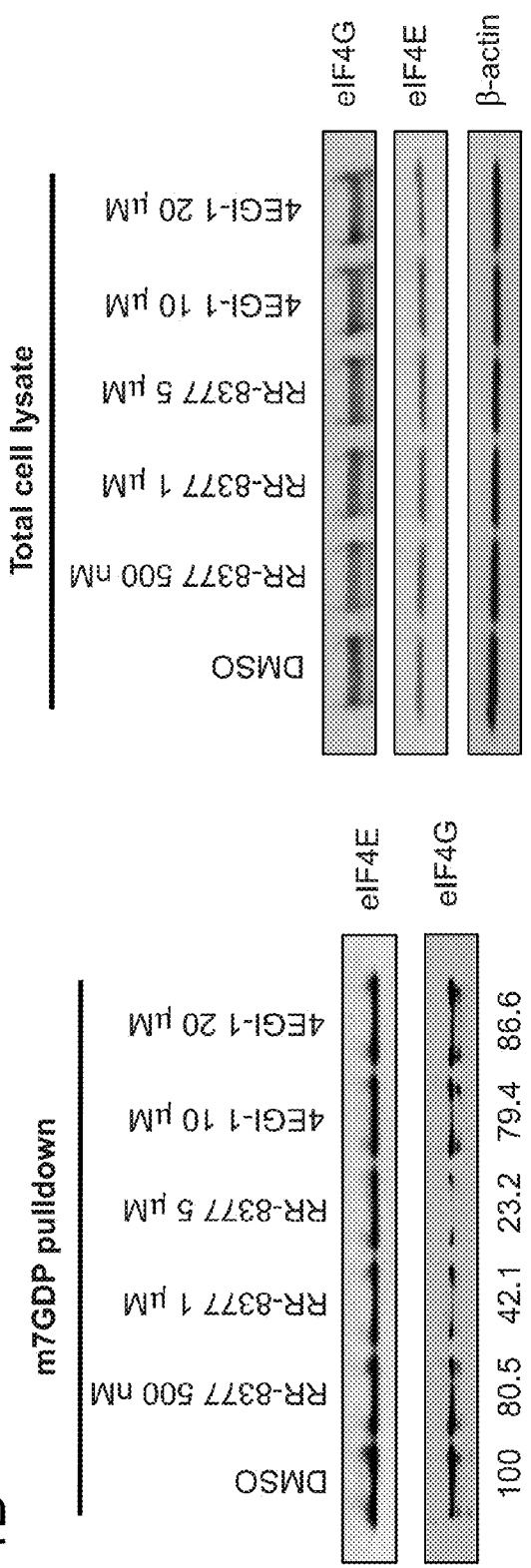
FIG. 1B depicts Western blot analysis of OCI-LY1 cells treated with DMSO, and multiple doses of RR-8377 or 4EGI-1.
Figure 1C:
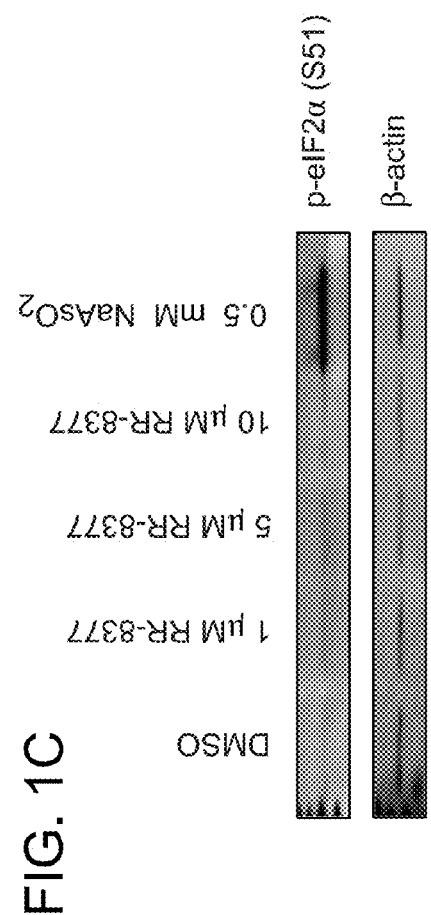
FIG. 1C depicts Western blot analysis of HeLa cells treated with either DMSO, multiple doses of RR-8377 or sodium arsenite.
Figure 1D:
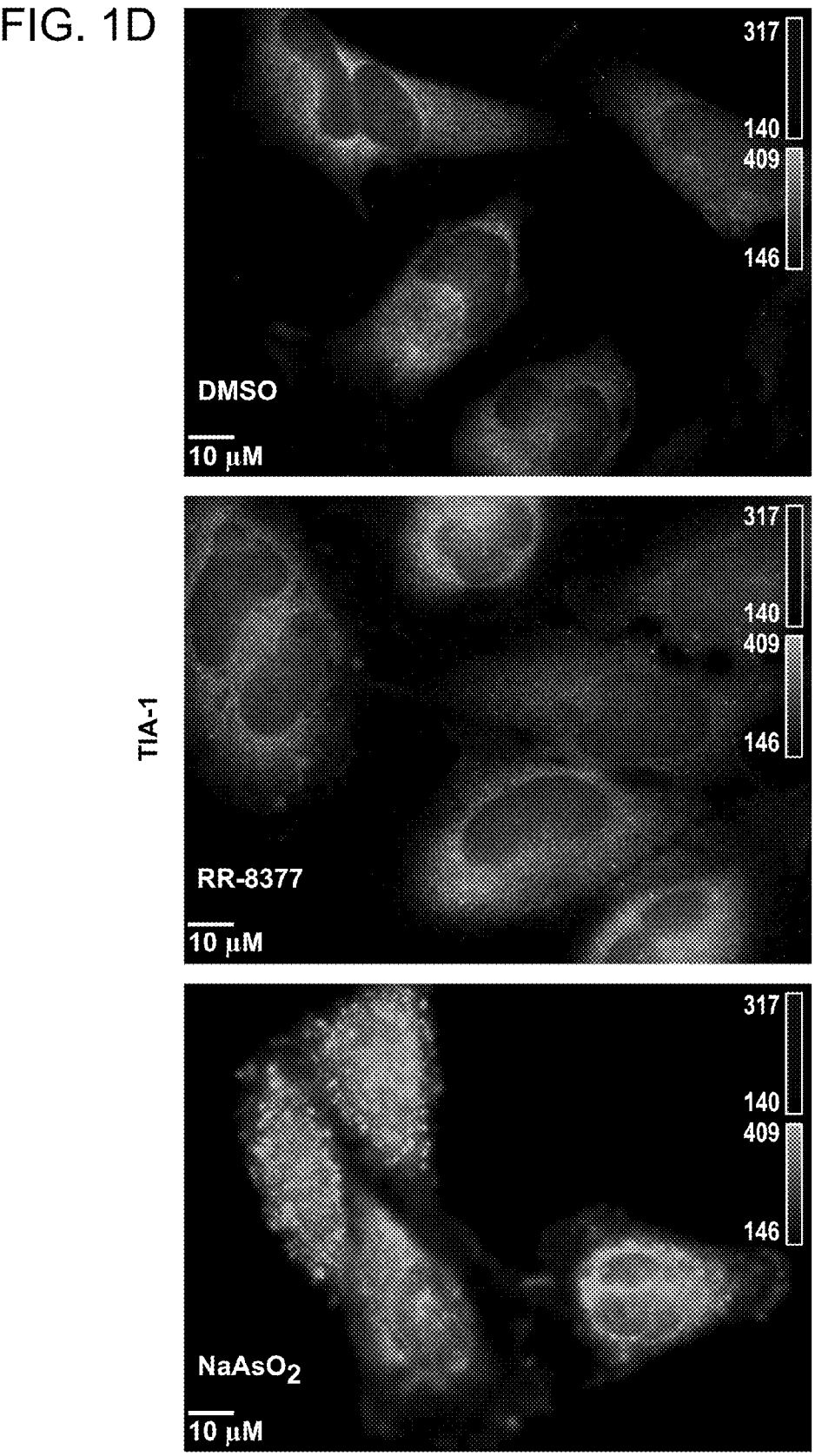
FIG. 1D depicts images of TIA-1 (green) or DNA (blue) monitored by immunofluorescence in HeLa cells treated with either DMSO, 5 µM RR-8377 (four hours) or 0.5 mM sodium arsenite (30 minutes).

It will be recognized that the results and examples in the figures are only illustrative and other examples and illustrations will be readily recognized by the person of ordinary skill in the art, given the benefit of this disclosure.

DETAILED DESCRIPTION OF CERTAIN EMBODIMENTS

In accordance with certain examples, compounds described herein inhibit translation (e.g., translation initiation). In accordance with certain examples, compounds described herein inhibit cellular proliferation. According to certain aspects compounds described herein inhibit interaction of eIF4E with eIF4G so as to inhibit translation initiation. According to certain aspects compounds described herein inhibit interaction of eIF4E with eIF4G so as to inhibit protein synthesis. According to certain aspects, compounds described herein disrupt eIF4F complex formation. According to certain aspects, compounds described herein reduce population of actively translating polysomes. According to certain aspects, compounds described herein induce apoptosis in malignant cells. According to certain aspects, compounds described herein induce apoptosis in malignant cells compared to normal diploid cells. According to certain aspects, compounds described herein are allosteric inhibitors to the extent that they induce a rearrangement on eIF4E upon binding that inhibits eIF4G association with eIF4E at a location other than the compounds binding site on eIF4E. Such compounds and methods are useful for the treatment of (1) proliferative disorders, (2) non-proliferative, degenerative disorders, (3) viral infections, (4) disorders associated with viral infections, and/or (5) non-proliferative metabolic disorders such as type II diabetes where inhibition of translation initiation is beneficial.

Certain examples are described below with reference to various chemical formulae. The chemical formulae referred to herein may exhibit the phenomena of tautomerism, conformational isomerism, stereo isomerism or geometric isomerism. As the formulae drawings within this specification can represent only one of the possible tautomeric, conformational isomeric, enantiomeric or geometric isomeric forms, it should be understood that the invention encompasses any tautomeric, conformational isomeric, enantiomeric or geometric isomeric forms which exhibit biological or pharmacological activity as described herein.

The compounds and compositions provided below are effective to inhibit translation (e.g., translation initiation) at least to the extent necessary for effective treatment of one or more cellular proliferative disorders and other disorders described herein. According to embodiments of the present invention, compounds of the present invention inhibit the protein-protein interaction between the eukaryotic translation initiation factors eIF4E and eIF4G, a translation initiation event commonly understood to be necessary for the proliferation of all cancer cells. According to aspects of the present invention, inhibition of translation initiation inhibits cell proliferation. According to embodiments of the present invention, cell proliferation is common to all forms of cancers and a method treating all forms of cancer is provided by inhibition of cellular proliferation.

While in certain examples, translation may be substantially inhibited such that little or no activity results, in other examples the inhibition is at least sufficient to relieve and or alleviate the symptoms from a selected disorder to be treated.

Certain compounds of the present invention are of the type set forth in the formulae provided herein. It is to be understood that substituents or moieties identified herein with respect to the structures presented throughout the specification may be bonded to atoms in a manner understood by those of skill in the art and that one or more moieties may include one or more acceptable bonding sites if not expressly indicated.

According to certain aspect, exemplary compounds within the scope of the present disclosure include those of Formula 1

Formula 1

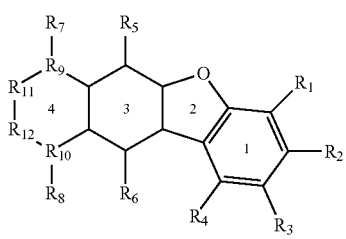

wherein R1 is hydrogen;
wherein R2 is hydroxyl or

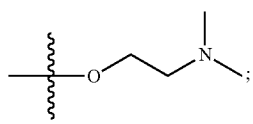 [SMILES: *OCCN(C)C]

or wherein R1 and R2 are connected and together is

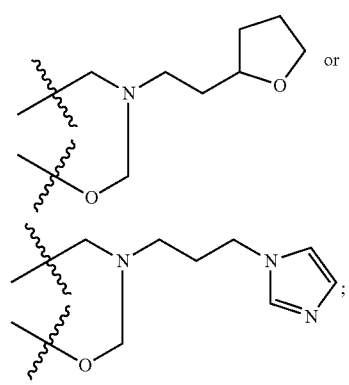

wherein R3 is hydrogen,
or wherein R2 and R3 are connected and together is

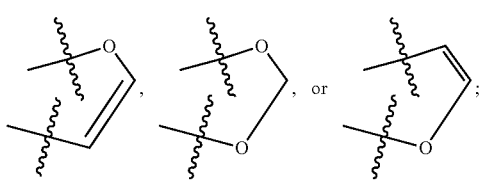

wherein R4 is hydrogen or hydroxyl;
wherein R5 is hydrogen, hydroxyl or a double bonded oxygen atom;
wherein ring structure 3 includes no double bonds, one double bond, two double bonds or three double bonds;
wherein R6 is hydrogen, hydroxyl or a double bonded oxygen atom;
wherein R7 hydrogen or hydroxyl;
wherein R8 is hydrogen or hydroxyl;
wherein R9 is a carbon atom or an oxygen atom, wherein if R9 is an oxygen atom, then R7 is absent;
wherein R10 is a carbon atom or an oxygen atom, wherein if R10 is an oxygen atom, then R8 is absent;
wherein R11 is a carbon atom;

wherein R12 is a carbon atom or an oxygen atom, wherein if R12 is an oxygen atom, then R11 is absent and ring 4 is a five membered ring; and
wherein ring 4 includes no double bonds, one double bond, two double bonds or three double bonds.

Exemplary compounds within the scope of the present disclosure include those of Formula 2

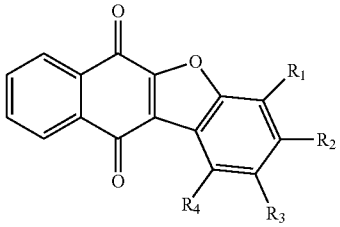

Formula 2 wherein R1 is hydrogen;
wherein R2 is hydroxyl or

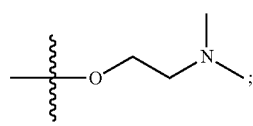 [SMILES: *OCCN(C)C]

or wherein R1 and R2 are connected and together is

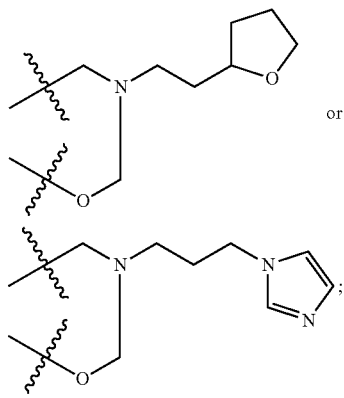

wherein R3 is hydrogen,
or wherein R2 and R3 are connected and together is

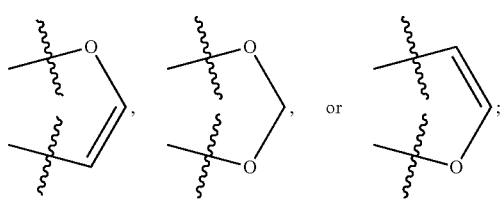 [SMILES: */C=C\O* ; *OCO* ; */C=C\O*]

and
wherein R4 is hydrogen or hydroxyl.

Exemplary compounds within the scope of the present disclosure include those of Formula 3

Formula 3

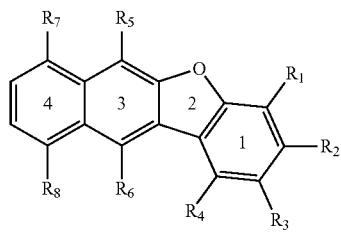

wherein R1 is hydrogen;
wherein R2 is hydroxyl or

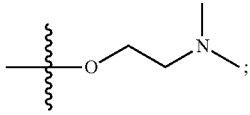

or wherein R1 and R2 are connected and together is

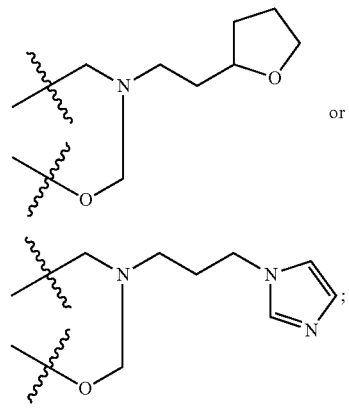

wherein R3 is hydrogen,
or wherein R2 and R3 are connected and together is

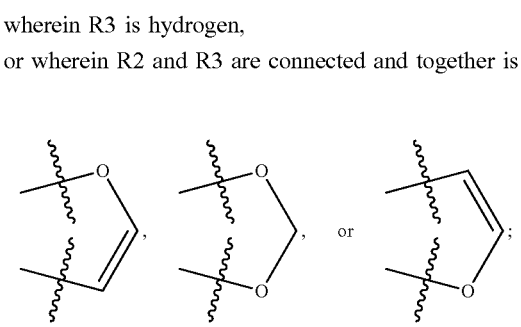

wherein R4 is hydrogen or hydroxyl;
wherein R5 is hydrogen or hydroxyl;
wherein R6 is hydrogen or hydroxyl;
wherein R7 hydrogen or hydroxyl; and
wherein R8 is hydrogen or hydroxyl.

Exemplary compounds within the scope of the present disclosure include those of Formula 4

Formula 4

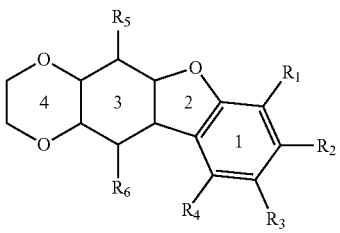

wherein R1 is hydrogen;
wherein R2 is hydroxyl or

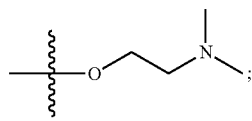 [SMILES: *OCCN(C)C]

or wherein R1 and R2 are connected and together is

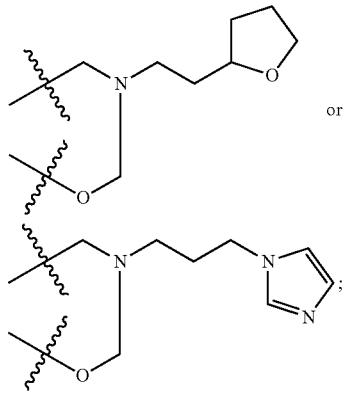

wherein R3 is hydrogen,
or wherein R2 and R3 are connected and together is

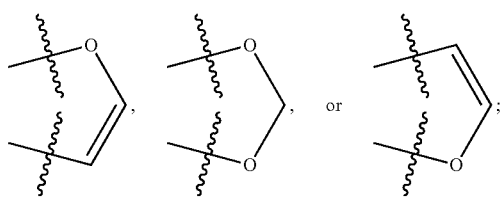

wherein R4 is hydrogen or hydroxyl;
wherein R5 is hydrogen, hydroxyl or a double bonded oxygen atom;
wherein ring structure 3 includes no double bonds, one double bond, two double bonds or three double bonds; and
wherein R6 is hydrogen, hydroxyl or a double bonded oxygen atom.

Exemplary compounds within the scope of the present disclosure include those of Formula 5

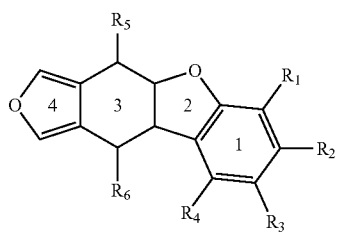

Formula 5 wherein R1 is hydrogen;
wherein R2 is hydroxyl or

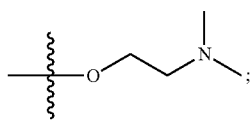 [SMILES: *OCCN(C)C]

or wherein R1 and R2 are connected and together is

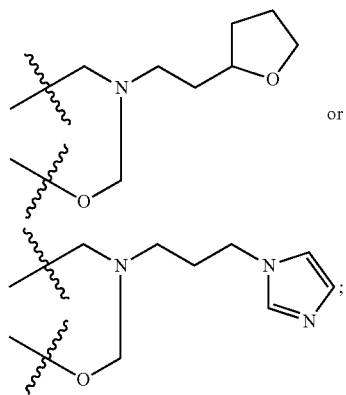

or wherein R3 is hydrogen,
or wherein R2 and R3 are connected and together is

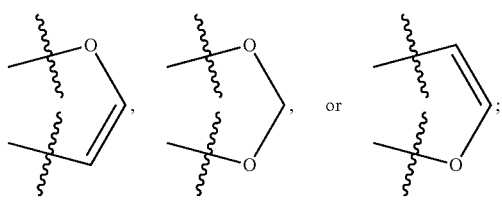 [SMILES: */C=C\O* ; *OCO* ; */C=C\O*]

, or ;

wherein R4 is hydrogen or hydroxyl;
wherein R5 is hydrogen, hydroxyl or a double bonded oxygen atom;
wherein ring structure 3 includes no double bonds, one double bond, two double bonds or three double bonds; and
wherein R6 is hydrogen, hydroxyl or a double bonded oxygen atom.

Exemplary representative compounds include the following:

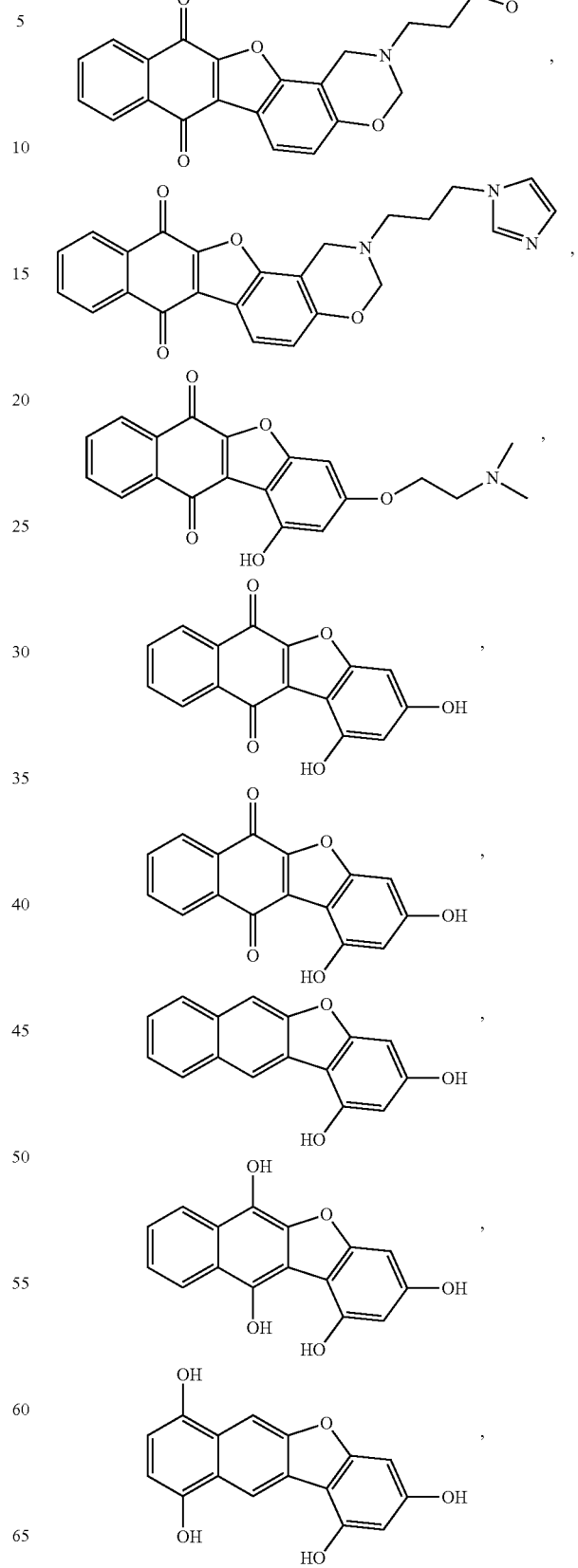

-continued

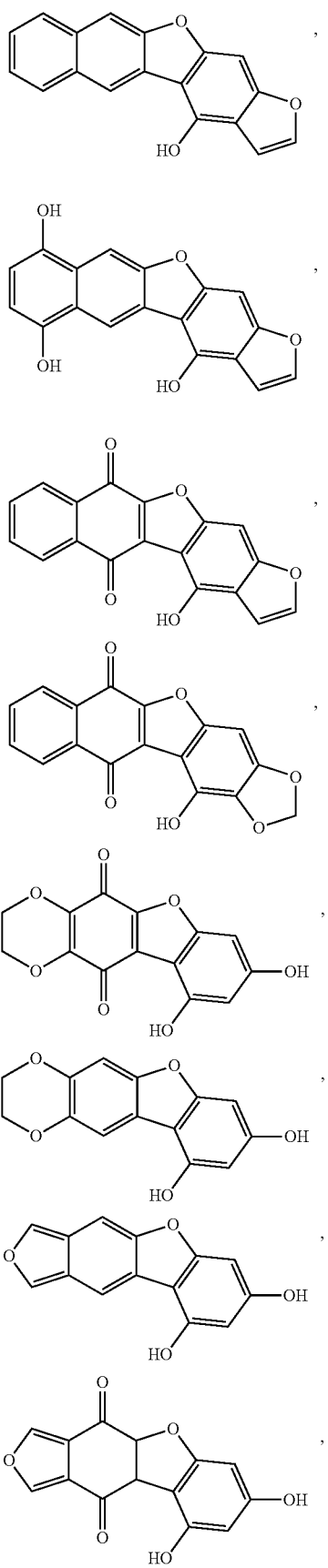

-continued

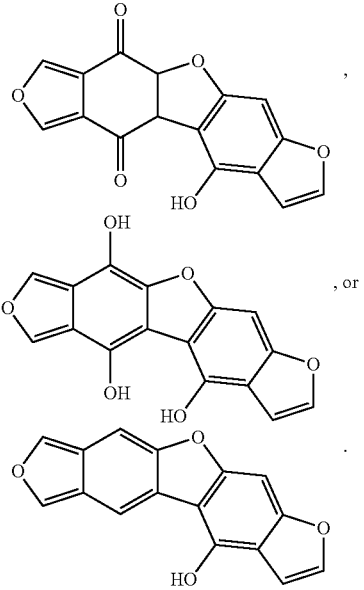

The structure of some of the compounds of the invention may contain one or more asymmetric carbon atoms. It is to be understood accordingly that the isomers arising from such asymmetry (e.g., all enantiomers and diastereomers) are included within the scope of the invention, unless indicated otherwise. Such isomers are obtained in substantially pure form by classical separation techniques and by stereochemically controlled synthesis. Furthermore, the structures and other compounds and moieties discussed in this application also include all tautomers thereof. Alkenes and imines can include either the E- or Z-geometry, where appropriate.

Embodiments of the present invention include salts of the compounds of the present disclosure. Solutions of active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Examples of acceptable salts include, but are not limited to, mineral or organic acid salts of basic residues such as amines; alkali or organic salts of basic residues such as carboxylic acids; and the like. The acceptable salts include the conventional non-toxic salts or the quaternary ammonium salts from non-toxic inorganic acids. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, mandelic, tartaric, citric, ascorbic, palmoic, maleic, hydroxymaleic, phenylacetic, glutamine, benzoic, salicylic, sulfanilic, 2-acteoxybenzoic, fumaric, toluenesulfonic, methanesulfonic, ethane disulfonic, oxalic, isethionic, and the like. Specifically, the acceptable salts can include those salts that naturally occur in vivo in a mammal. According to certain embodiments, preferred salts include chloride, bromide, iodide and fluoride.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc. San Diego, Calif., 1992, pp. 19-23). A particularly preferred anionic group is a carboxylate.

The present invention also features a method of inhibiting cap-dependent protein synthesis in a cell by contacting the cell with one or more of the compounds described herein. This inhibition in turn causes apoptosis, which results from the downregulation of growth-promoting proteins as well as the upregulation of apoptosis-promoting proteins and IRES-dependent proteins (e.g., Apaf-1, c-myc, XIAP, and DAP5).

During apoptosis, 4E-BP1 undergoes caspase-dependent cleavage of its first 24 amino acids. The N-terminal segment that is eliminated contains a RAIP motif, which is needed to start phosphorylation. Thus, the truncated form of 4E-BP1 binds tightly to eIF4E but is not efficiently phosphorylated. The ectopic expression of eIF4E protects cells from apoptosis whereas the overexpression of 4E-BP1 can induce apoptosis in transformed cells. Treatment of cultured cells with synthetic peptides containing the eIF4E-binding motif fused to a penetratin sequence has been shown to induce apoptosis.

The compounds described herein are useful to inhibit protein synthesis thereby inhibiting proliferation of a cell such as a tumor cell or an abnormal cell (benign or malignant cell). An abnormal cell is a cell having an increased proliferation index, a decreased apoptotic index, or both relative to a normal non-cancerous cell. For example, the compounds, referred to as inhibitory compounds, preferentially or selectively inhibit tumor cell growth compared to normal cell growth. For example, protein synthesis and/or cell proliferation is inhibited at least 10%, 25%, 50%, 75%, 100%, and up to 5-fold, 10-fold and more in tumor cells compared to non-tumor cells. The method is carried out by administering to a patient in need thereof a pharmaceutical composition containing the inhibitory compound. According to one aspect, the patient or animal to be treated is identified as one that has a tumor cell containing an increased level of a cap-dependent translation initiation factor compared to the level in a normal non-tumor cell. For example, the patient is diagnosed as having a tumor or abnormal proliferating cells which is characterized by an increased amount of a cap-dependent translation factor compared to the level in a normal non-tumor cell. For example, the tumor cell contains an aberrantly high amount of eIF4E and/or eIF4G. Such tumor types include tumors of the lung, breast, skin, bone, head (neurological tissues such as brain and spinal cord), neck, bladder, colon, prostate, ovaries, uterus, cervix, larynx, gallbladder, pancreas, rectum, parathyroid, thyroid, adrenal gland, kidney, bronchi, liver, gastrointestinal tract, lymphomas, and neuroblastomas.

Cells according to the present disclosure also include stem cells and stem-like cells. Cancer stem cells (CSCs) are tumor subpopulation cells that recur and propagate tumors in a hierarchical fashion (Al-Hajj et al., 2003; Anderson et al., 2010; Curtis et al., 2010; Gupta et al., 2009; Hong et al., 2008; Mani et al., 2008). CSC-enriched cancer cell subpopulations exhibit certain characteristic properties: (i) initiation of tumors in vivo at limiting dilutions; (ii) expression of specific cell markers, such as CD44high/CD24low in certain mammary CSCs; (iii) formation of a spherical colony (termed tumor mammospheres or tumorspheres) in suspension cultures in vitro; and (iv) enhanced resistance to common therapeutic modalities such as chemotherapy and irradiation (Shackleton et al., 2009). Currently, CSCs have been isolated from several human tumors including leukemia (Lapidot et al., 1994), breast (Al-Hajj et al., 2003), melanoma (Schatton et al., 2008), pancreatic cancer (Hermann et al., 2007), and myelodysplasia (Tehranchi et al., 2010). The presence of these tumor subpopulations correlates strongly with tumor recurrence and treatment failure in patients. Cancer stem cells are known to exist in the well-established perivascular niche around tumor vasculature, however it has recently been proposed that CSCs may exist in a secondary hypoxic niche within cancers that is further away from vasculature and, as a consequence, is more hypoxic (Keith and Simon, 2007). Synergistic effects have been observed between hypoxia/HIF-1α and DLK1, Notch/Delta/Serrate family member, mechanistically linking hypoxia and CSCs (Kim et al., 2009). Low oxygen tension, even as low as 0.2%, increased HIF-1α protein levels in glioma stem cells (Mohyeldin et al., 2010). Clinical studies have shown that hypoxia (0.02-5% O2) is associated with increased tumor burden and a more aggressive phenotype in solid tumors. Hypoxic tumors are resistant to standard therapies, difficult to eradicate, and thus lead to poor overall patient survival (Harris, 2002). The precise mechanisms of hypoxic tumors, particularly the hypoxic effects on CSC self-renewal and proliferation at the hypoxic niche, have yet to be fully determined.

One or more compounds of the invention may be administered with one or more pharmacologically active agents. The one or more compounds of the invention may be administered with the one or more pharmacologically active agents to a patient simultaneously, sequentially, or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms, which are taken simultaneously. The term "combination" further refers to the case where the compounds or additional pharmacologically active agent are provided in separate dosage forms and are administered sequentially.

Combination therapy" (or "co-therapy") includes the administration of a compound of the invention and at least a second agent (each referred to as a therapeutic agent) as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, inhalation, oral routes, intravenous routes, intramuscular routes, subcutaneous, rectal, intraperitoneal, parenteral, transdermal, gastrointestinal, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, therapeutic agents may be administered orally or by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In at least certain examples, the compounds disclosed here can be used in the treatment of cellular proliferative disorders, such as cancer or non-cancer proliferative disorders. Treatment of cellular proliferative disorders is intended to include, but is not limited to, inhibition of proliferation including rapid proliferation. As used herein, the term "cellular proliferative disorder" includes, but is not limited to, disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Id. Such abnormal tissue shows partial or complete lack of structural organization and functional coordination with the normal tissue, which may be either benign (i.e., benign tumor) or malignant (i.e., malignant tumor).

The language "treatment of cellular proliferative disorders" is intended to include, but is not limited to, the prevention of the growth of neoplasms in a subject or a reduction in the growth of pre-existing neoplasms in a subject. The inhibition also can be the inhibition of the metastasis of a neoplasm from one site to another. In certain embodiments, the neoplasms are sensitive to the compounds of the present invention. Examples of the types of neoplasms intended to be encompassed by the present invention include, but are not limited to, those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, and/or kidneys.

Examples of general categories of cancer include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells. In adults most often found in the testicle or ovary; in fetuses, babies and young children, most often found on the body midline, particularly at the tip of the tailbone), blastic tumors (i.e., a typically malignant tumor which resembles an immature or embryonic tissue) and the like.

Examples of specific neoplasms or cancers intended to be encompassed by the present invention include, but are not limited to, acute lymphoblastic leukemia; myeloid leukemia, acute myeloid leukemia, childhood; adrenocortical carcinoma; AIDS-related cancers; AIDS-related lymphoma; anal cancer; appendix cancer; astrocytoma (e.g., cerebellar, cerebral); atypical teratoid/rhabdoid tumor; basal cell carcinoma; bile duct cancer, extrahepatic; bladder cancer; bone cancer, osteosarcoma and malignant fibrous histiocytoma; brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors); breast cancer; bronchial tumors; Burkitt lymphoma; carcinoid tumor (e.g., gastrointestinal); carcinoma of unknown primary; central nervous system (e.g., atypical teratoid/rhabdoid tumor, embryonal tumors (e.g., lymphoma, primary); cerebellar astrocytoma; cerebral astrocytoma/malignant glioma; cervical cancer; chordoma; chronic lymphocytic leukemia; chronic myelogenous leukemia; chronic myeloproliferative disorders; colon cancer; colorectal cancer; craniopharyngioma; cutaneous T-cell lymphoma; embryonal tumors, central nervous system; endometrial cancer; ependymoblastoma; ependymoma; esophageal cancer; Ewing family of tumors; extracranial germ cell tumor; extragonadal germ cell tumor; extrahepatic bile duct cancer; eye cancer (e.g., intraocular melanoma, retinoblastoma); gallbladder cancer; gastric cancer; gastrointestinal tumor (e.g., carcinoid tumor, stromal tumor (gist), stromal cell tumor); germ cell tumor (e.g., extracranial, extragonadal, ovarian); gestational trophoblastic tumor; glioma (e.g., brain stem, cerebral astrocytoma); hairy cell leukemia; head and neck cancer; hepatocellular cancer; Hodgkin lymphoma; hypopharyngeal cancer; hypothalamic and visual pathway glioma; intraocular melanoma; islet cell tumors; Kaposi sarcoma; kidney cancer; large cell tumors; laryngeal cancer (e.g., acute lymphoblastic, acute myeloid); leukemia (e.g., acute myeloid, chronic lymphocytic, chronic myelogenous, hairy cell); lip and/or oral cavity cancer; liver cancer; lung cancer (e.g., non-small cell, small cell); lymphoma (e.g., AIDS-related, Burkitt, cutaneous T-cell, Hodgkin, non-Hodgkin, primary central nervous system); macroglobulinemia, Waldenström; malignant fibrous histiocytoma of bone and/or osteosarcoma; medulloblastoma; medulloepithelioma; melanoma; merkel cell carcinoma; mesothelioma; metastatic squamous neck cancer; mouth cancer; multiple endocrine neoplasia syndrome; multiple myeloma/plasma cell neoplasm; mycosis fungoides; myelodysplastic syndromes; myelodysplastic/myeloproliferative diseases; myelogenous leukemia (e.g., chronic, acute, multiple); myeloproliferative disorders, chronic; nasal cavity and/or paranasal sinus cancer; nasopharyngeal cancer; neuroblastoma; non-Hodgkin lymphoma; non-small cell lung cancer; oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor); pancreatic cancer (e.g., islet cell tumors); papillomatosis; paranasal sinus and/or nasal cavity cancer; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma cell neoplasm/multiple myeloma; pleuropulmonary blastoma; primary central nervous system lymphoma; prostate cancer; rectal cancer; renal cell cancer; renal, pelvis and/or ureter, transitional cell cancer; respiratory tract carcinoma involving the nut gene on chromosome 15; retinoblastoma; rhabdomyosarcoma; salivary gland cancer; sarcoma (e.g., Ewing family of tumors, Kaposi, soft tissue, uterine); Sézary syndrome; skin cancer (e.g., non-melanoma, melanoma, merkel cell); small cell lung cancer; small intestine cancer; soft tissue sarcoma; squamous cell carcinoma; squamous neck cancer with occult primary, metastatic; stomach cancer; supratentorial primitive neuroectodermal tumors; T-cell lymphoma, cutaneous; testicular cancer; throat cancer; thymoma and/or thymic carcinoma; thyroid cancer; transitional cell cancer of the renal, pelvis and/or ureter; trophoblastic tumor; unknown primary site carcinoma; urethral cancer; uterine cancer, endometrial; uterine sarcoma; vaginal cancer; visual pathway and/or hypothalamic glioma; vulvar cancer; Waldenström macroglobulinemia; Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

Examples of noncancerous cellular proliferative disorders includes fibroadenoma, adenoma, intraductal papilloma, nipple adenoma, adenosis, fibrocystic disease or changes of breast, plasma cell proliferative disorder (PCPD), restenosis, atherosclerosis, rheumatoid arthritis, myofibromatosis, fibrous hamartoma, granular lymphocyte proliferative disorders, benign hyperplasia of prostate, heavy chain diseases (HCDs), lymphoproliferative disorders, psoriasis, idiopathic pulmonary fibrosis, scleroderma, cirrhosis of the liver, IgA nephropathy, mesangial proliferative glomerulonephritis, membranoproliferative glomerulonephritis, hemangiomas, vascular and non-vascular intraocular proliferative disorders and the like. One of skill in the art will understand that this list is exemplary only and is not exhaustive, as one of skill in the art will readily be able to identify additional noncancerous cellular proliferative disorders based on the disclosure herein.

In accordance with certain other examples, methods for treating viral infections are also disclosed. Treatment of viral infections is intended to include, but is not limited to, the use of a compound described herein to prevent the initiation of viral protein synthesis. The term "viral infection," as used herein, refers to one or more cells which have been infected with a virus, such as a DNA or RNA animal virus. As used herein, RNA viruses include, but are not limited to, virus families such as picornaviridae (e.g., polioviruses), reoviridae (e.g., rotaviruses), togaviridae (e.g., encephalitis viruses, yellow fever virus, rubella virus), orthomyxoviridae (e.g., influenza viruses), paramyxoviridae (e.g., respiratory syncytial virus, measles virus, mumps virus, parainfluenza virus), rhabdoviridae (e.g., rabies virus), coronaviridae, bunyaviridae, flaviviridae, filoviridae, arenaviridae, bunyaviridae, and retroviridae (e.g., human T-cell lymphotropic viruses (HTLV), human immunodeficiency viruses (HIV)). As used herein, DNA viruses include, but are not limited to, virus families such as papovaviridae (e.g., papilloma viruses), adenoviridae (e.g., adenovirus), herpesviridae (e.g., herpes simplex viruses), and poxviridae (e.g., variola viruses). In certain embodiments, the viral infection is caused by hepatitis B virus, hepatitis C virus, and/or HIV. One of skill in the art will understand that this list is exemplary only and is not exhaustive, as one of skill in the art will readily be able to identify additional viral infections based on the disclosure herein.

In accordance with other examples, methods for treating disorders associated with viral infections are disclosed. Treatment of one or more disorders associated with viral infections is intended to include, but is not limited to, the use of a compound described herein to reduce or alleviate one or more symptoms of a viral infection. As used herein, the term "disorders associated with viral infection" refers to the host's response to infection by one or more viruses.

Such responses include, but are not limited to neurological symptoms (e.g., encephalitis, meningoencephalitis, paralysis, myelopathy, neuropathy, aseptic meningitis, hemiparesis, dementia, dysphagia, lack of muscular coordination, impaired vision, coma, and the like), wasting symptoms (e.g., inflammatory cell infiltration, perivascular cuffing of blood vessels, demyelination, necrosis, reactive gliosis and the like), gastroenteritis symptoms (e.g., diarrhea, vomiting, cramps and the like), hepatitis symptoms (nausea, vomiting, right upper quadrant pain, raised liver enzyme levels (e.g., AST, ALT and the like), jaundice and the like), hemorrhagic fever symptoms (e.g., headache, fever, chills body pains, diarrhea, vomiting, dizziness, confusion, abnormal behavior, pharyngitis, conjunctivitis, red face, red neck, hemorrhage, organ failure and the like), oncogenic symptoms (e.g., sarcomas, leukemias and the like, as well as "rare" malignancies, e.g., Kaposi's sarcoma, oral hairy leukoplasia, lymphomas and the like), immunodeficiency symptoms (e.g., opportunistic infections, wasting, rare malignancies, neurological disease, fever, diarrhea, skin rashes and the like), lesions (e.g., warts (e.g., common wart, flat wart, deep hyperkaratotic palmoplantar wart, superficial mosaic type palmoplantar wart and the like), epidermodysplasia, mucosal lesions, ulcers and the like), and systemic symptoms (e.g., fever, chills, headache, muscle pain, bone pain, joint pain, pharyngitis, tonsillitis, sinusitis, otitis, bronchitis, pneumonia, bronchopneumonia, nausea, vomiting, increased salivation, rash, macules, lymphadenopothy, arthritis, ulcers, photosensitivity, weight loss, irritability, restlessness, anxiety, coma, death and the like). Disorders associated with viral infections are described in Fields Virology 4th Ed. (2001) Lippincott, Williams & Wilkins, and the introduction to medical virology website (web.uct.ac.za/depts./mmi/jmoodie/introvi2.html), incorporated herein by reference in their entirety for all purposes. One of skill in the art will understand that this list is exemplary only and is not exhaustive, as one of skill in the art will readily be able to identify additional disorders associate with viral infections based on the disclosure herein.

In accordance with other examples, methods for treating non-proliferative, degenerative disorders associated with aberrant translation initiation using a compound described herein to alleviate and/or reduce one or more symptoms associated with a non-proliferative, degenerative disorder are disclosed. Treatment of non-proliferative, degenerative diseases are intended to include, but is not limited to, the use of compounds described herein. As used herein, the term "non-proliferative degenerative disorder" is intended to include, but is not limited to, diseases characterized by a loss of function of cells, tissues, and/or organs due to aberrant translation initiation. See Gkogkas et al., Autism-related deficits via dysregulated eIF4E-dependent translational control, doi:10.1038/nature11628 (2012); Santini et al., "Exaggerated translation causes synaptic and behavioral aberrations associated with autism, doi:10.1038/nature11782 (2012). "Non-proliferative degenerative disorders" include neurodevelopmental conditions and disorders and neurodegenerative conditions and disorders characterized by a loss of function of cells, tissues, and/or organs due to aberrant translation initiation. Neurodevelopmental conditions or disorders include autism, autism spectrum disorders, attention deficit disorder, attention deficit hyperactivity disorder, attention deficit disorder not otherwise specified, obsessive compulsive disorder, Asperger syndrome, pervasive developmental disorder, pervasive developmental disorder not otherwise specified, social communication disorder, stereotypic movement disorder, intellectual development deficit, adaptative behavior disorder, developmental coordination disorder, developmental coordination disorder not otherwise specified, developmental language disorder, social interaction developmental disorder, learning developmental disorder, learning developmental disorder not otherwise specified, chronic motor or vocal tic disorder, La Tourette's syndrome, tics not otherwise specified, restricted repetitive patterns of behavior disorder, deficits in attention deficit, motor control and perception, Rourke's syndrome, Gillberg's syndrome Lorna Wing's syndrome, Kanner's syndrome, and multiple complex developmental disorder. Neurodegenerative conditions and disorders include degenerative disorders of the brain, degenerative disorders of the nerves and disorders of myelin. Exemplary neurodegenerative conditions and disorders include Alzheimer's disease, frontotemporal dementia, dementia with Lewy bodies, corticobasal degeneration, progressive supranuclear palsy, prion disorders, Parkinson's disease, Huntington's disease, multiple system atrophy, amyotrophic lateral sclerosis, inclusion body myositis, degenerative myopathy, hereditary spastic paraparesis, spinocerebellar atrophies, Friedreich's ataxia, amyloidosis, metabolic disorders, diabetes, diabetic neuropathy, metabolic neuropathy, endocrine neuropathy, orthostatic hypotension, multiple sclerosis, and Charcot Marie Tooth disease. Certain exemplary non-proliferative degenerative disorders include, but are not limited to, disorders such as Alzheimer's disease, atherosclerosis, arthritis, keloid scars, psoriasis and insulin resistance. One of skill in the art will understand that these lists are exemplary only and are not exhaustive, as one of skill in the art will readily be able to identify additional non-proliferative degenerative disorders based on the disclosure herein.

In accordance with other examples, methods for treating disorders characterized by unwanted synthesis and/or abnormal accumulation of one or more mutant and/or wild-type proteins are provided. Treatment of one or more disorders associated with unwanted synthesis and/or abnormal accumulation is intended to include, but is not limited to, the use of a compound of the present invention to reduce or alleviate one or more symptoms characterized by unwanted synthesis and/or abnormal accumulation. Without intending to be bound by scientific theory, contacting a subject afflicted with a disorder characterized by unwanted synthesis and/or abnormal accumulation of one or more mutant and/or wild-type proteins with a compound described herein (e.g., a compound that can inhibit translation initiation) can reduce the load on the protein-folding machinery and, accordingly, may reduce the severity of the disorder. Disorders associated with unwanted synthesis and/or abnormal accumulation of one or more mutant and/or wild-type proteins include, but are not limited to, Tay-Sachs disease, cystic fibrosis, phenylketonuria, Fabry disease, Alzheimer's disease, Huntington's disease, Parkinson's disease, congophilic angiopathy, prion related disorders (i.e., transmissible spongiform encephalopathies such as Creutzfeldt-Jacob disease, kuru, fatal familial insomnia, scrapie, bovine spongiform encephalopathy and the like) and the like. One of skill in the art will understand that this list is exemplary only and is not exhaustive, as one of skill in the art will readily be able to identify additional disorders characterized by unwanted synthesis and/or abnormal accumulation of one or more mutant and/or wild-type proteins based on the disclosure herein.

In accordance with certain other examples, kits for treating one or more (1) proliferative disorders, (2) non-proliferative, degenerative disorders, (3) viral infections, (4) disorders associated with viral infections, and/or (5) non-proliferative metabolic disorders such as type II diabetes where inhibition of translation initiation is beneficial, are provided. In one example, the kit may comprise one or more compounds of the present invention, or a combination of one or more compounds of the present invention. In another example, the kit may comprise a pharmaceutically acceptable carrier. In an additional example, the kit may also include instructions for treating (1) proliferative disorders, (2) non-proliferative, degenerative disorders, (3) viral infections, (4) disorders associated with viral infections, and/or (5) non-proliferative metabolic disorders such as type II diabetes where inhibition of translation initiation is beneficial. In some examples, the kit may also comprise, e.g., a buffering agent, a preservative, or a protein stabilizing agent. In other examples, the kit may also contain a control sample or a series of control samples, which can be assayed and compared to the test sample contained. Other suitable components for including in the kit will be selected by the person of ordinary skill in the art, given the benefit of this disclosure.

In accordance with certain examples, compounds of the present invention can be incorporated into pharmaceutical compositions suitable for administration. Such compositions typically comprise the compounds disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, transdermally, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

In accordance with other examples, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMPHOR EL™ (BASF, Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In accordance with other examples, sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation can be vacuum drying and freeze-drying which yields a powder of the active ingredient plus any additional desired ingredient from a previously sterile-filtered solution thereof. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In at least certain examples, the one or more compounds disclosed herein are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811, incorporated herein by reference in its entirety for all purposes.

According to certain exemplary embodiments, the compounds of the present invention can be chemically modified to include or attach polyethylene glycol (PEG) to the compound in a process referred to as PEGylation. Specific advantages of PEGylation include increased efficacy, reduced dosing frequency, reduced toxicity, reduced immunogenicity, reduced side effects, increased stability, increased shelf-life, increased half-life and enhanced solubility. The compounds may be PEGylated directly or through a linker according to the methods known to those of skill in the art such as Davis, Adv. Drug Deliv. Rev. 54, 457-458 (2002), Veronese, Bioorg. Med. Chem. Lett, 12, 177-180 (2002), Harris, Adv. Drug. Deliv. Rev. 54, 459-476 (2002), Chapman, Nature Biotechnology 17, 780-783 (1999), and Sato, Adv. Drug Deliv. Rev. 54, 487-504 (2002) hereby incorporated by reference in their entireties and other references readily available to those of skill in the art. Similarly, the compounds can be chemically glysocylated insofar as saccharides are linked to the compound using methods known to those of skill in the art. Examples of glycosylation include N-linked glycosylation and O-linked glycosylation. Specific advantages of glysocylation include increased efficacy, reduced dosing frequency, reduced toxicity, reduced immunogenicity, reduced side effects, increased stability, increased shelf-life, increased half-life and enhanced solubility. Further embodiments of the compounds include dimers, trimers, oligomers, etc. thereof. It is to be understood that modifications of the compounds of the present invention include modifications, chemical, physical or otherwise, to a core compound used by those of skill in the art to increase efficacy, reduce dosing frequency, reduced toxicity, reduced immunogenicity, reduced side effects, increased stability, increased shelf-life, increased half-life and enhanced solubility such as PEGylation or glycosylation or dimerization other methods known to those of skill in the art.

In accordance with certain examples, pharmaceutical compositions of the invention comprise one or more compounds of the present invention covalently linked to a peptide (i.e., a polypeptide comprising two or more amino acids). Peptides may be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments can also be obtained by sequential assembly from amino acids or by fragment coupling of still shorter peptides.

In both sequential assembly and fragment coupling it is necessary to link the units (e.g., amino acids, peptides, compounds and the like) by forming an amide linkage, which can be accomplished via a variety of enzymatic and chemical methods. The methods described herein for formation of peptidic amide linkages are also suitable for the formation of non-peptidic amide linkages.

Chemical methods for forming the amide linkage are described in detail in standard references on peptide chemistry, including Muller, Methoden der organischen Chemie Vol. XV/2, 1-364, Thieme Verlag, Stuttgart, (1974); Stewart and Young, Solid Phase Peptide Synthesis, 31-34 and 71-82, Pierce Chemical Company, Rockford, Ill. (1984); Bodanszky et al., Peptide Synthesis, 85-128, John Wiley & Sons, New York, (1976); Practice of Peptide Synthesis, M. Bodansky, A. Bodansky, Springer-Verlag, 1994 and other standard works in peptide chemistry, incorporated herein by reference in their entirety for all purposes. Methods include the azide method, the symmetric and mixed anhydride method, the use of in situ generated or preformed active esters, the use of urethane protected N-carboxy anhydrides of amino acids and the formation of the amide linkage using coupling reagents, such as dicyclohexylcarbodiimide (DCC), diisopropylcarbodiimide (DIC), 1-ethoxycarbonyl-2-ethoxy-1,2-dihydroquinoline (EEDQ), pivaloyl chloride, 1-ethyl-3-(3-dimethylaminopropyl)carbodiimide hydrochloride (EDCI), n-propane-phosphonic anhydride (PPA), N,N-bis (2-oxo-3-oxazolidinyl)amido phosphoryl chloride (BOP—Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N',N'-tetramethyluronium salts (HBTU), O-azabenzotriazolyl-N,N,N',N'-tetramethyluronuim salts (TATU), diethylphosphoryl cyanide (DEPCN), 2,5-diphenyl-2,3-dihydro-3-oxo-4-hydroxythiophene dioxide (Steglich's reagent; HOTDO), 1,1'-carbonyldiimidazole (CDI) and the like. The coupling reagents can be employed alone or in combination with additives such as N,N-dimethyl-4-aminopyridine (DMAP), N-hydroxy-benzotriazole (HOBt), N-hydroxybenzotriazine (HOOBt), N-hydroxysuccinimide (HOSu), 2-hydroxypyridine and the like.

In accordance with other examples, methods of modulating translation initiation for therapeutic purposes are disclosed. In one example, a method involves contacting a cell with an agent that inhibits translation initiation. An agent that inhibits translation initiation can be any one of the compounds described herein. In at least certain examples, the compound modulates or otherwise inhibits the interaction of eIF4E and eIF4G. Methods of modulating translation initiation can be performed in vitro (e.g., by culturing a cell with the agent) or, alternatively, in vivo (e.g., by administering the agent to a subject). Certain examples disclosed herein are directed to methods of treating an individual afflicted with a disease or disorder characterized by aberrant translation initiation. Examples of such disorders are described herein. In one embodiment, the method involves administering a compound or a combination of compounds describe herein that inhibits translation initiation. As used herein, an individual afflicted with a disease or disorder is intended to include both human and non-human mammals. Examples of non-human mammals include, but are not limited to, non-human primates, horses, cows, goats, sheep, dogs, cats, mice, rats, hamsters, guinea pigs and the like.

The present invention provides for both prophylactic and therapeutic methods of treating a subject for one or more (1) proliferative disorders, (2) non-proliferative, degenerative disorders, (3) viral infections, (4) disorders associated with viral infection, and/or (5) nonproliferative metabolic disorders such as type II diabetes where inhibition of translation initiation is beneficial. In one aspect, the invention provides a method for preventing in a subject, a disease or condition associated with one or more (1) proliferative disorders, (2) non-proliferative, degenerative disorders, (3) viral infections, (4) disorders associated with viral infection, and/or (5) nonproliferative metabolic disorders such as type II diabetes where inhibition of translation initiation is beneficial by administering, to the subject one or more compounds described herein to modulate one or more (1) proliferative disorders, (2) non-proliferative, degenerative disorders, (3) viral infections, (4) disorders associated with viral infection, and/or (5) nonproliferative metabolic disorders such as type II diabetes where inhibition of translation initiation is beneficial. Administration of a prophylactic agent can occur prior to the manifestation of symptoms, such that a disease or disorder is prevented or, alternatively, delayed in its progression.

Another aspect of the invention pertains to therapeutic methods of treating one or more (1) proliferative disorders, (2) non-proliferative, degenerative disorders, (3) viral infections, (4) disorders associated with viral infection for therapeutic purposes, and/or (5) nonproliferative metabolic disorders such as type II diabetes where inhibition of translation initiation is beneficial. Accordingly, in an exemplary embodiment, a therapeutic method of the invention involves contacting a subject with one or more compounds described herein that therapeutically treats one or more (1) proliferative disorders, (2) non-proliferative, degenerative disorders, (3) viral infections, (4) disorders associated with viral infection and/or (5) nonproliferative metabolic disorders such as type II diabetes where inhibition of translation initiation is beneficial.

One embodiment of the present invention involves a method of treating a translation initiation-associated disease or disorder, which includes the step of administering a therapeutically and/or prophylactically effective amount of a compound, which inhibits translation initiation to a subject. In another embodiment, a subject is administered a therapeutically and/or prophylactically effective amount that is effective to inhibit interaction of eIF4E and eIF4G. As defined herein, a therapeutically and/or prophylactically effective amount of agent (i.e., an effective dosage) ranges from about 0.001 to 30 mg/kg body weight, from about 0.01 to 25 mg/kg body weight, from about 0.1 to 20 mg/kg body weight, from about 1 to 10 mg/kg, from about 2 to 9 mg/kg, from about 3 to 8 mg/kg, from about 4 to 7 mg/kg, or from about 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Treatment of a subject with a therapeutically and/or prophylactically effective amount of an inhibitor can include a single treatment or can include a series of treatments. It will also be appreciated that the effective dosage of in used for treatment may increase or decrease over the course of a particular treatment.

EXAMPLE 1

Cell Culture

Diffuse Large B-Cell Lymphoma (OCI-LY1 and OCI-LY7), acute T-cell leukemia (Jurkat), chronic myelogenous leukemia (K562), and acute myelogenous leukemia (MOLM-13) cells were cultured in RPMI-1640 containing 10% fetal bovine serum and 1% Penicillin/Streptomycin. Cervical carcinoma (HeLa) and non-small cell lung cancer (A549) cells were cultured in Dulbecco's modified essential medium containing 10% fetal bovine serum and 1% Penicillin/Streptomycin. Normal diploid lung tissue (WI-38) cells were cultured in Eagle's Minimum Essential Medium containing 10% fetal bovine serum and 1% Penicillin/Streptomycin. The plasmid used to express BCL-XL was generated in the laboratory of Dr. Stanley Korsmeyer and purchased from Addgene (plasmid #8749).

EXAMPLE 2

Synthesis Protocols

The procedure for the preparation of benzonaphthofurandiones was performed as described in J. Med. Chem. 36(25): 4108-4112. All melting points were taken in Pyrex capillaries using electrothermal digital melting point apparatus (Buchi, New Castle, Del.). 1H NMR spectra were recorded on a 500 MHz Bruker NMR spectrometer. Samples were dissolved DMSO-d6. Mass spectra were obtained on a 6130 Quadrupole LC-Mass spectrometer (Agilent, Santa Clara, Calif.). TLC was carried out on silica gel (Merck-60F-254) using Hexanes:Ethyl acetate (2:3) as eluent, with visualization at 254 and 366 nm. Purification of compounds were performed using glass columns of 10 cm length, and 1 cm diameter using Sigma-Aldrich silica gel Grade 9385, pore size 60A, 230-400 mesh.

1,3-Dihydroxybenzo[b]naphtho[2,3-d]furan-6,11-dione (RST-69): To a stirred solution of 31.5 mL of MeOH containing 1.26 g (0.0225 M) of KOH was added portionwise at 30° C. to 1.02 g (0.0045 M) of powdered 2,3-dichloro-1,4-naphthoquinone. After 15 minutes, the mixture appeared as a red crystalline suspension. This mixture was added dropwise with continuous stirring to a 10% methanolic solution of 0.85 g (0.0068 M) of phloroglucinol. The color of the reaction mixture gradually changed from red to blue black and then to dark brown. After stirring for 5 hours at room temperature, TLC examination indicated total consumption of the starting material. The separated solids were collected by filtration and washed thoroughly with MeOH, followed by the treatment of more than 0.2 N HCl at 0° C. The resulting dark brown solid product was collected by filtration (the pH of the filtrate should be less than 3, an indication of total acidification), washed with EtOH, and dried in a vacuum at 60° C. The product was recrystallized from DMF to give 0.54 g (51% yield) of analytically pure RST-69 as dark brown needles, mp 341-343° C. dec; 1H-NMR δ (DMSO-d6) 6.36 (s, 1H, ArH), 6.36 (s, 1H, ArH), 7.85-8.0 (m, 2H, ArH), 8.05-8.15 (m, 2H, ArH), 9.65 (s, 1H, OH), 10.5 (s, 1H, OH); MS (rel. intensity): m/z 280.8 ([M+1]+, 100).

3-[2-(Diethylamino)ethoxy]-1-hydroxybenzo[b]naphtho [2,3-d]furan-6,11-dione (RST-73): To a suspension of 0.14 g (0.5 mM) of RST-69 in 10 mL of CHCl3 was added a solution of 0.21 g (1.5 mM) of K2CO3 in 1 mL of H2O followed by 0.17 g (1 mM) of 2-(diethylamino)ethyl chloride hydrochloride in 1 mL of H2O. The mixture was refluxed overnight with vigorous stirring. The solution was cooled and the organic phase was separated. The aqueous portion was extracted with CHCl3 (2×5 mL). The combined organic phase was washed with brine and H2O and dried on Na2SO4. Evaporation of the solvent followed by column chromatography gave 0.115 g (60% yield) of pure RST-73 as brick red crystals upon recrystallization from BuOH—CHCl3, mp 198-199° C.; 1H-NMR δ (DMSO-d6) 2.2 (s, 6H, CH3), 2.6 (t, 2H, CH2), 4.15 (t, 2H, CH2), 6.47 (s, 1H, ArH), 7.0 (s, 1H, ArH), 7.82-7.97 (m, 2H, ArH), 8.05-8.17 (m, 2H, ArH), 9.70 (s, 1H, OH), 10.5 (s, 1H, OH); MS (rel. intensity): m/z 351.8 ([M+1]+, 100): 3-[2-(Diethylamino) ethoxy]-1-hydroxybenzo[b]naphtho[2,3-d]furan-6,11-dione (RST-73) was acidified in EtOH—HCl to yield the hydrochloride salt as black crystals after recrystallization from BuOH—HCONMe2; mp 262-264° C.

EXAMPLE 3

Western Blotting and Statistical Analysis

Western blots were carried out as described in Blood 117(8):2441-2450. Briefly, 4-20% SDS-PAGE was performed on 10-50 μg of protein. Protein gels were then transferred to PVDF membranes. Blots were probed with antibodies recognizing: eIF4E, α-Tubulin, eIF4G, BCL-XL, p-eIF2α (S51) (Cell Signaling, Beverly, Mass.), Caspase 3, cleaved PARP, β-actin (Abcam, Cambridge, Mass.). Signals were detected with enhanced chemiluminescence according to manufacturer's instructions (Pierce, Rockford, Ill.). Densitometric analysis was performed using Adobe Photoshop CS5 software (Adobe, San Jose, Calif.). Statistical analysis of results was perfoemed with Microspft Excel (Microsoft, Redmond, Wash.).

EXAMPLE 4

7-methyl-GDP Sepharose Pulldown

Following four hours of treatment with DMSO, RR-8377 or 4EGI-1, cells were lysed with radio immunoprecipitation assay (RIPA) buffer, and lysates were used for pull-down with 7-methyl-GDP cap analog Sepharose beads. Following washes with NT2 buffer (50 mM Tris-HCl (pH 7.4), 150 mM NaCl, 1 mM MgCl2, and 0.05% Nonidet P-40) beads were incubated with SDS loading buffer. Pull-down reactions were resolved by sodium dodecyl sulfate-polyacrylamide gel electrophoresis (SDS-PAGE) gels and analyzed by immunoblotting for eIF4E and eIF4G.

EXAMPLE 5

Polysome Preparation and Q-PCR

HeLa, Jurkat, OCI-LY1 cells were collected by centrifugation and resuspended in Buffer 3 containing 5 mM Tris-HCl (pH 7.4), 2.5 mM MgCl2 (pH 7.5), 1.5 mM KCl, 1% Triton X-100, 0.5% Sodium Deoxycholate, 2 mM DTT and 200 u/mL RNasin as described in Blood 117(8):2441-2450. Lysates were pelleted (16,400×g, 5 minutes, 4° C.), and the cytoplasmic extracts were then loaded onto 10-50% sucrose gradients and centrifuged (Beckman SW41, 35,000 rpm, 3 hours, 4° C.). Subsequently, the material was fractionated into 1 ml aliquots using a gradient fractionator and RNA levels were monitored with an in-line photospectrometer at an absorbance of 254 nm. RNA from polysomal fractions or total RNA was extracted with Trizol reagent (Invitrogen, Carlsbad, Calif.). RNA from total or polysome fractions was reverse transcribed by using qScript cDNA synthesis kit (Quanta BioSciences, Gaithersburg, Md.) and the resulting cDNA was amplified by quantitative real-time PCR (qPCR) analysis using gene-specific primer pairs: catttaggggc-cactttga and tttggactgggagtgaggac for BCL-XL, or ggc-caaggtacagagagctg and cacgtttggcatacatcagg for α-Tubulin mRNA. An Applied Biosystems 7900HT Fast Real-Time PCR System (Applied Biosystems, Carlsbad, Calif.) and PerfeCTa SYBR Green SuperMix, ROX (Quanta BioSciences, Gaithersburg, Md.) were used to carry out the qPCR analysis.

EXAMPLE 6

Protein Expression and NMR Experiments

The fusion protein GB1-eIF4E was constructed as described in Cell 128(2):257-267. eIF4E protein samples were expressed in *Escherichia coli* in LB or isotopically labeled M9 media, then purified by cap-affinity chromatography on m7GDP agarose resin. Protein samples for NMR were prepared in a buffer composed of 50 mM sodium phosphate, 100 mM potassium chloride, and 1 mM DTT at pH 6.5. STD measurements were performed on a Bruker 500 MHz spectrometer employing a pulse scheme with water suppression and T1ρ filters. The irradiation power ($\gamma B1/2\pi$) was 20 Hz, which was applied on-resonance at 0 ppm or off-resonance at −10 ppm. The spectra were collected in an interleaved fashion to reduce temporal fluctuations. The relaxation delay was set to 60 seconds to allow the anesthetic ligands to relax between on- and off-resonance irradiation cycles. The STD spectrum collected at each tsat was the sum of 128 scans. For NMR chemical shift perturbation experiments, two-dimensional 15N HSQC were collected on a 600-MHz Bruker spectrometer using 175 µM 15N-labeled GB1-m4E with m7GDP in a 1:2 molar ratio with various small molecule inhibitors or DMSO-d6 at a probe temperature of 18° C. All NMR data were processed using NMRPipe.

EXAMPLE 7

Tryptophan Fluorescence

In order to determine the dissociation constant (Kd), the intrinsic fluorescence properties of the tryptophan residues in eIF4E were utilized. m7GDP bound eIF4E was incubated with increasing concentrations of RR-8377, and the emission of tryptophan (344 nm) was measured.

EXAMPLE 8

Discussion

FIG. 1: Compound RR-8377 alters polysomal loading and disrupts eIF4F complex formation. A) Cytoplasmic lysates from HeLa, Jurkat, and OCI-LY1 cells treated with DMSO or multiple doses of RR-8377 for four hours or Puromycin for 30 minutes, were fractionated through sucrose gradient centrifugation and absorbance of 254 nm was measured. From left to right, the distribution of free mRNA (not bound to ribosomes or ribosome subunits), ribosome subunits 40S and 60S, as well as 80S monosomes (single ribosomes) and polysomes of increasing molecular weight is indicated. B) OCI-LY1 cells were treated with DMSO, and multiple doses of RR-8377 or 4EGI-1. A total of 1000 µg of cell lysates were incubated with m7GDP cap analog conjugated to agarose beads and used to analyze bound eIF4G. Total eIF4E, eIF4G and β-actin levels were measured by Western blot analysis. C) HeLa cells were treated with either DMSO or multiple doses of RR-8377. Levels of peIF2α (S51) or β-actin were measured by Western blot analysis. D) TIA-1 or DNA were monitored by immunofluorescence in HeLa cells treated with either DMSO, 5 µM RR-8377 (four hours) or 0.5 mM sodium arsenite (30 minutes).

Figure 2:
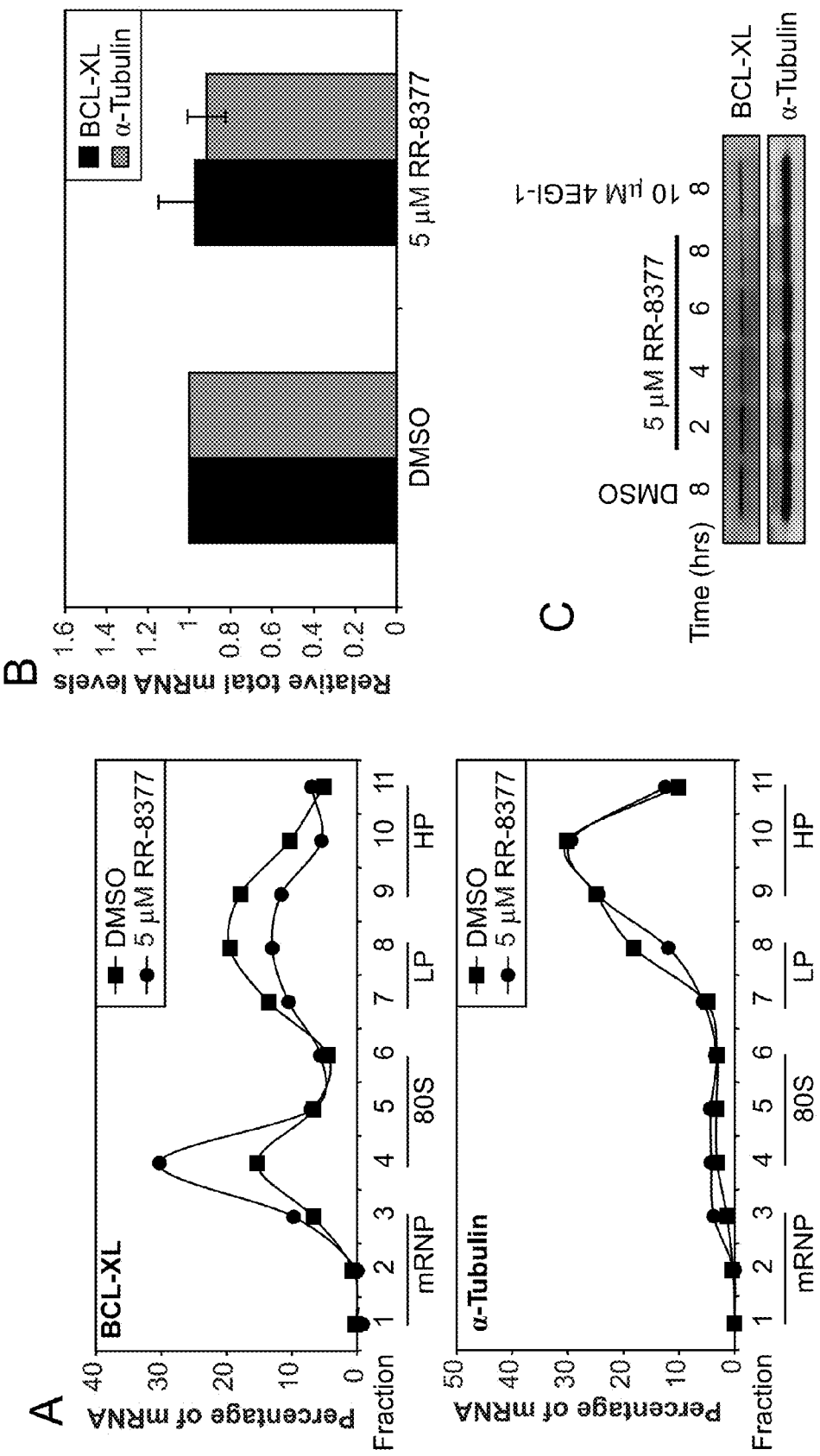
FIG. 2A depicts graphical data of HeLa cells were treated with DMSO or 5 µM RR-8377 for four hours.
FIG. 2B depicts graphical data of cytoplasmic lysates from either DMSO (square) or RR-8377 (circle) treated HeLa cells.
FIG. 2C depicts Western blot analysis of HeLa cells treated with DMSO, 5 µM RR-8377, and 10 µM 4EGI-1 for indicated time points.

FIG. 2: RR-8377 inhibits translation of BCL-XL mRNA. A) HeLa cells were treated with DMSO (square) or 5 µM RR-8377 (circle) for four hours. Following sucrose gradient centrifugation, quantitative PCR was performed on RNA isolated from each fraction using specific primers for BCL-XL or α-tubulin. Data for each fraction are represented as the percentage of the total mRNA from either DMSO or RR-8377 treated cells. Cytoplasmic fractions are grouped together as free messenger ribonucleoprotein (mRNP), 80S ribosomes, and light (LP) or heavy (HP) polysomes. B) Cytoplasmic lysates from either DMSO or RR-8377 treated HeLa cells were collected. Quantitative PCR was performed on the RNA isolated from total cytoplasmic lysates using specific primers for BCL-XL and α-tubulin. C) Western blot analysis of HeLa cells treated with DMSO, 5 µM RR-8377, and 10 µM 4EGI-1 for indicated time points. Abundance of BCL-XL and α-tubulin were assessed.

Figure 3A:
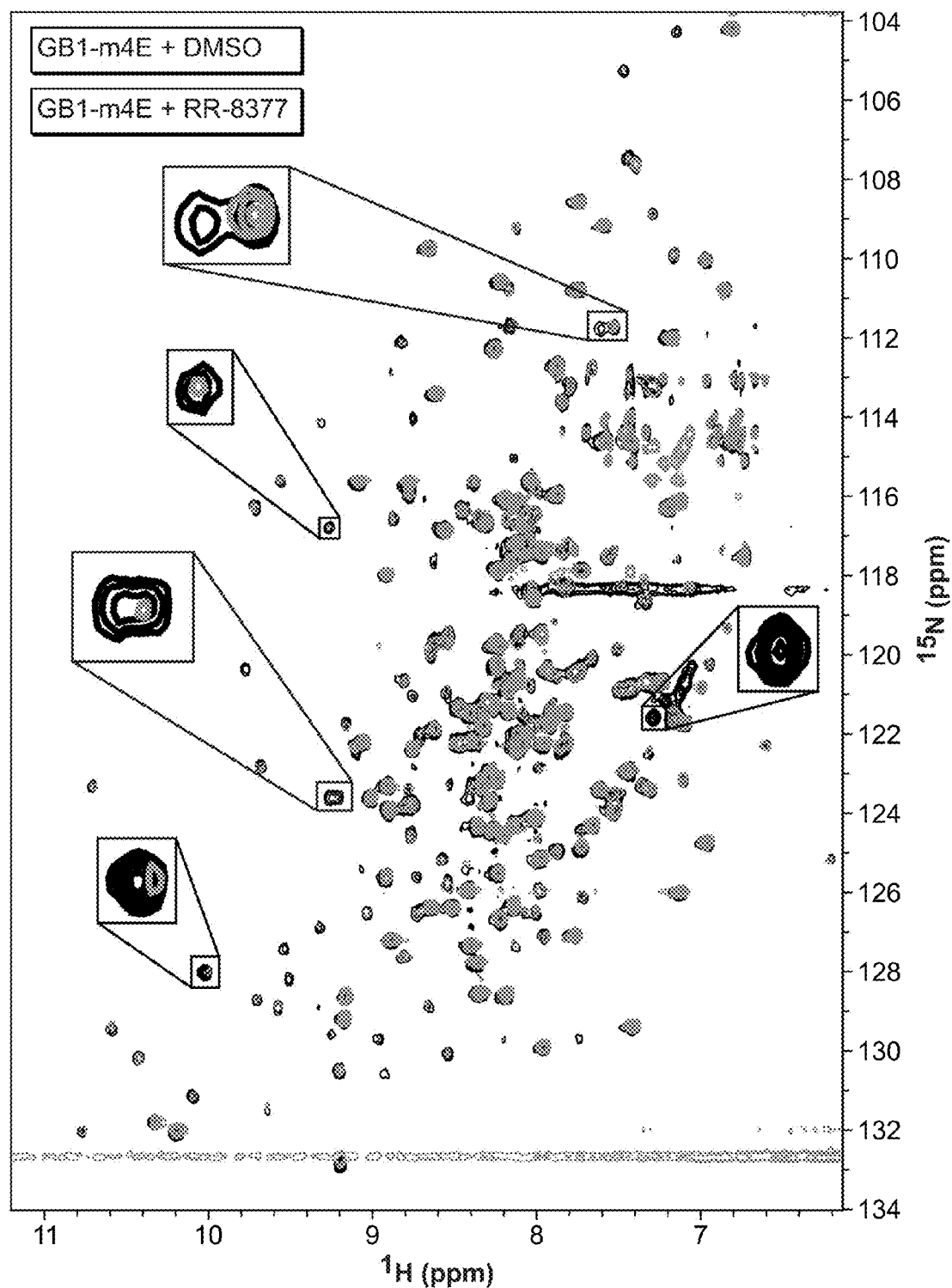
FIG. 3A depicts an overlay of HSQC spectra of GB1-m4E:DMSO-D6 in black and a complex of GB1-m4E:RR-8377 in gray (in the molar ratio of 1:2).
Figure 3B:
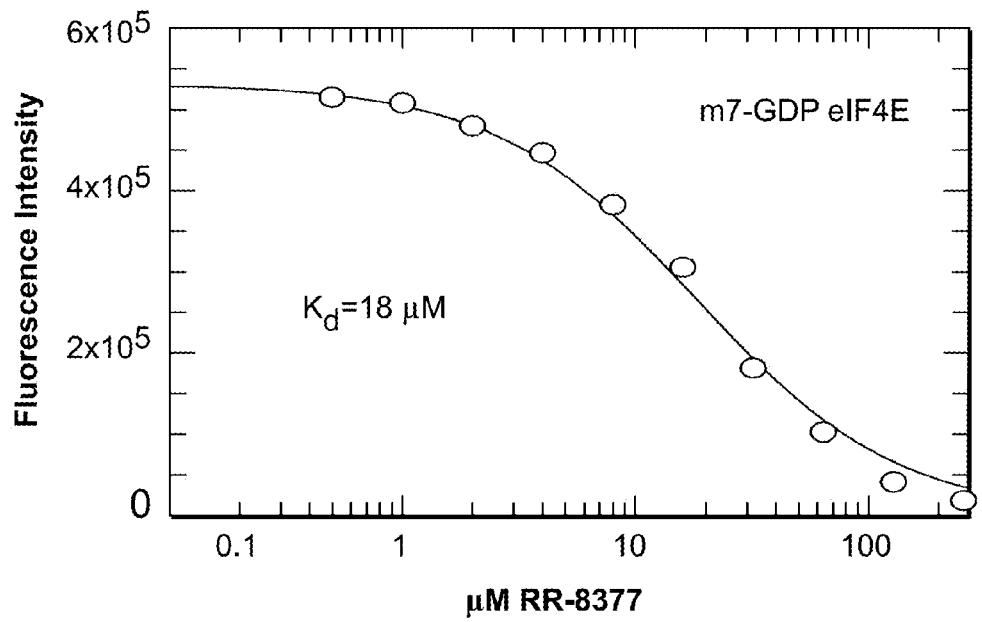
FIG. 3B depicts graphical data of the binding of RR-8377 to m7GDP-eIF4E measured by monitoring fluorescence intensity upon titration of RR-8377.

FIG. 3: RR-8377 interacts with eIF4E and induces structural rearrangements in eIF4E protein. A) Overlay of HSQC spectra of GB1-m4E:DMSO-D6 in black and a complex of GB1-m4E:RR-8377 in gray (in the molar ratio of 1:2). B) The binding of RR-8377 to m7GDP-eIF4E was measured by monitoring fluorescence intensity upon titration of RR-8377.

Figure 4A:
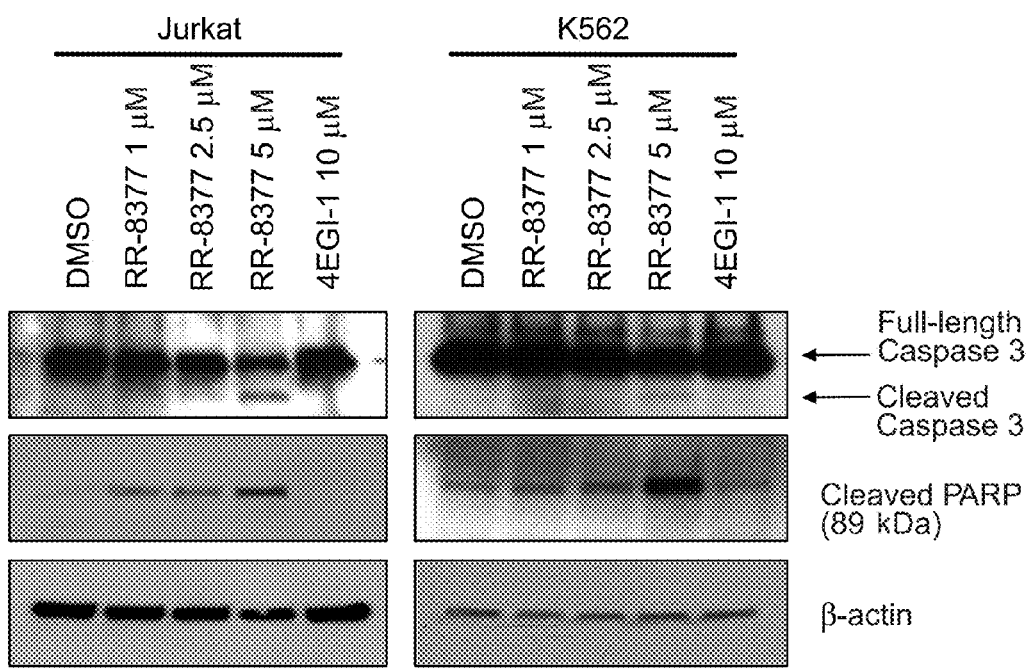
FIG. 4A depicts Western blot analysis of Jurkat and K562 cells treated with DMSO, RR-8377 or compound 4EGI-1 for twenty-four hours.
Figure 4B:
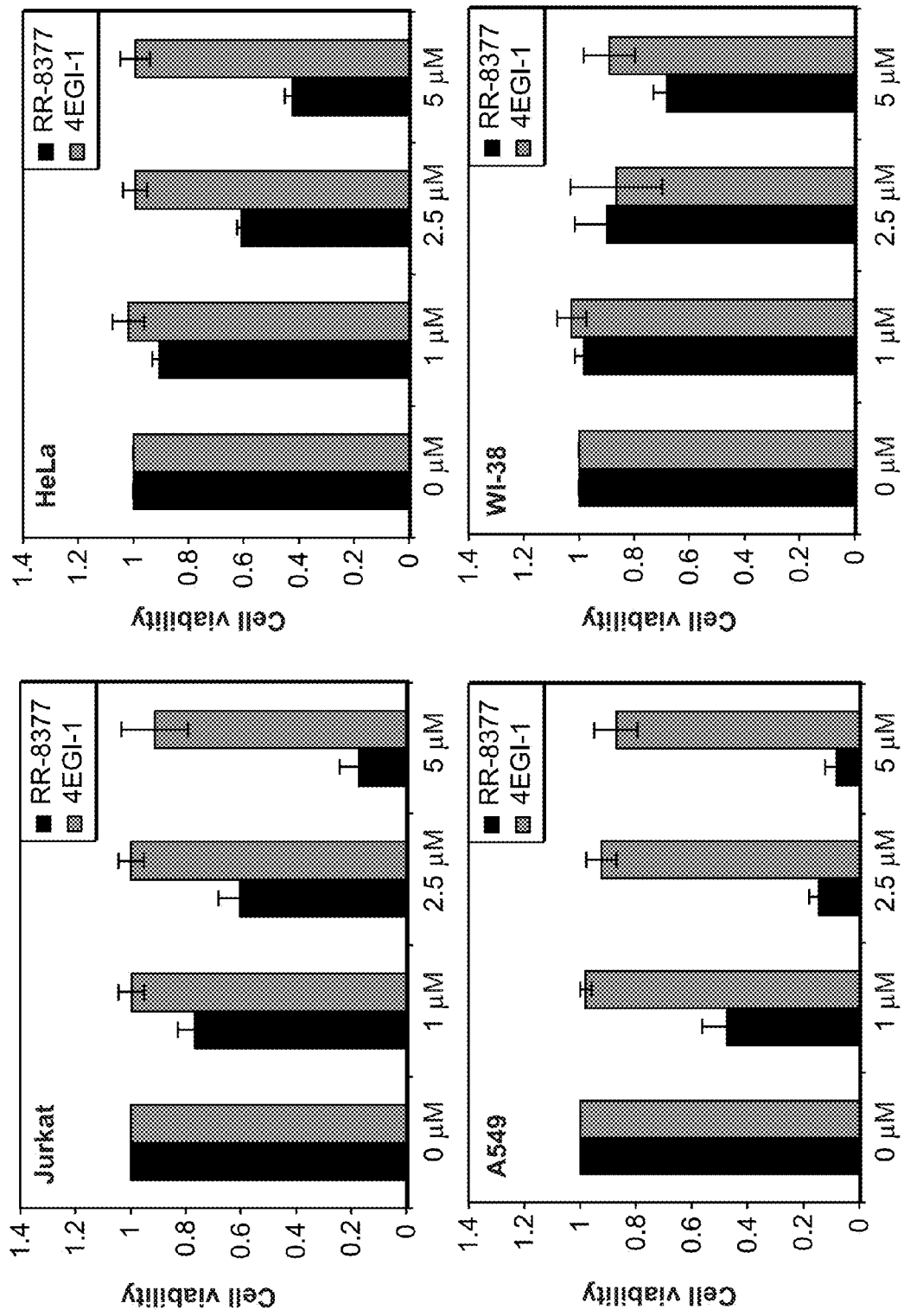
FIG. 4B depicts graphical data of cell viability of Jurkat, HeLa, A549 and WI-38 cells treated with RR-8377 and 4EGI-1 for twenty-four hours assessed via measuring ATP consumption (Cell Titre Glo, Promega) according to manufacturer's instructions.
Figure 4C:
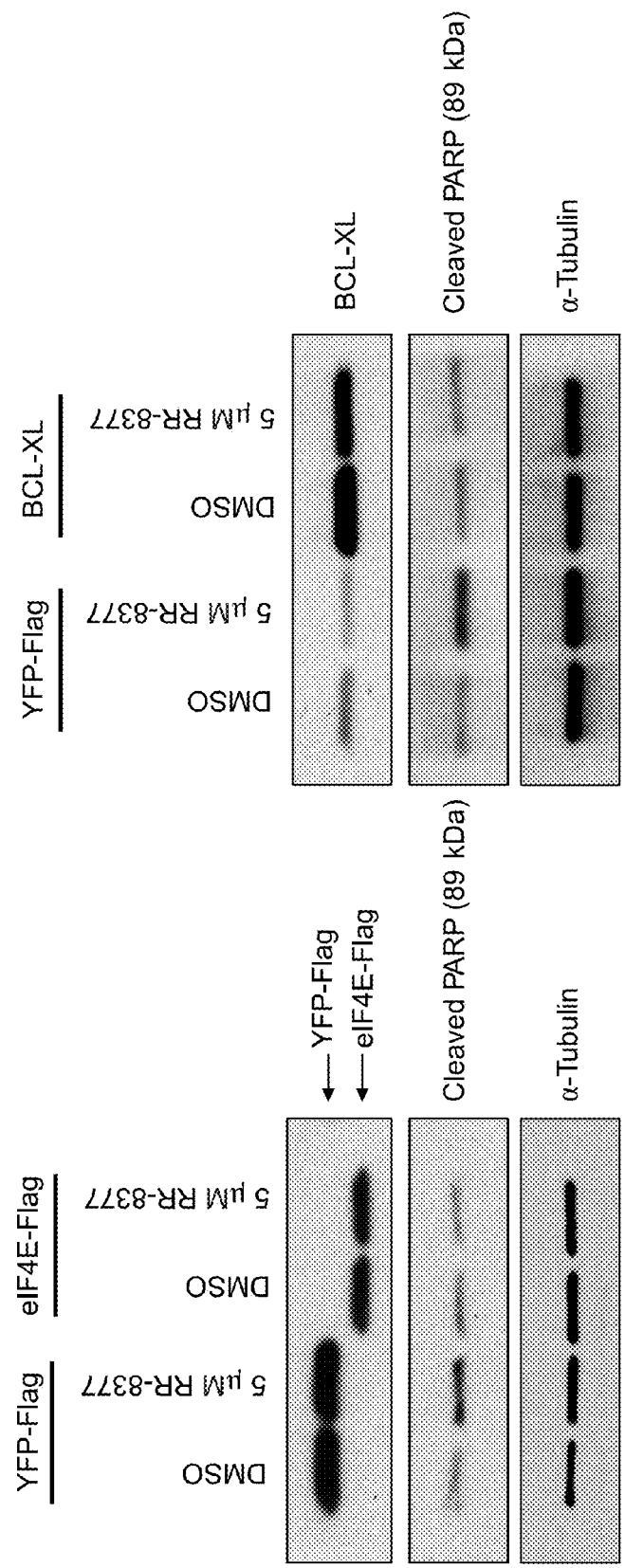
FIG. 4C depicts Western blot analysis of HeLa cells transfected with YFP-Flag, eIF4E-Flag or BCL-XL and treated with DMSO or 5 µM RR-8377 for twenty-four hours.

FIG. 4: Inhibition of eIF4F complex formation induces apoptosis in multiple cancer cell lines. A) Western blot analysis of Jurkat and K562 cells treated with DMSO, RR-8377 or compound 4EGI-1 for twenty-four hours. Abundance of Caspase-3, cleaved Poly (ADP-ribose) polymerase (PARP) and β-actin were assessed. B) Cell viability of Jurkat, HeLa, A549 and WI-38 cells treated with RR-8377 and 4EGI-1 for twenty-four hours was assessed via measuring ATP consumption (Cell Titre Glo, Promega) according to manufacturer's instructions. C) Western blot analysis of HeLa cells transfected with YFP-Flag, eIF4E-Flag or BCL-XL and treated with DMSO or 5 µM RR-8377 for twenty-four hours. Abundance of Flag, BCL-XL, cleaved PARP and α-tubulin were assessed.

Figure 5B:
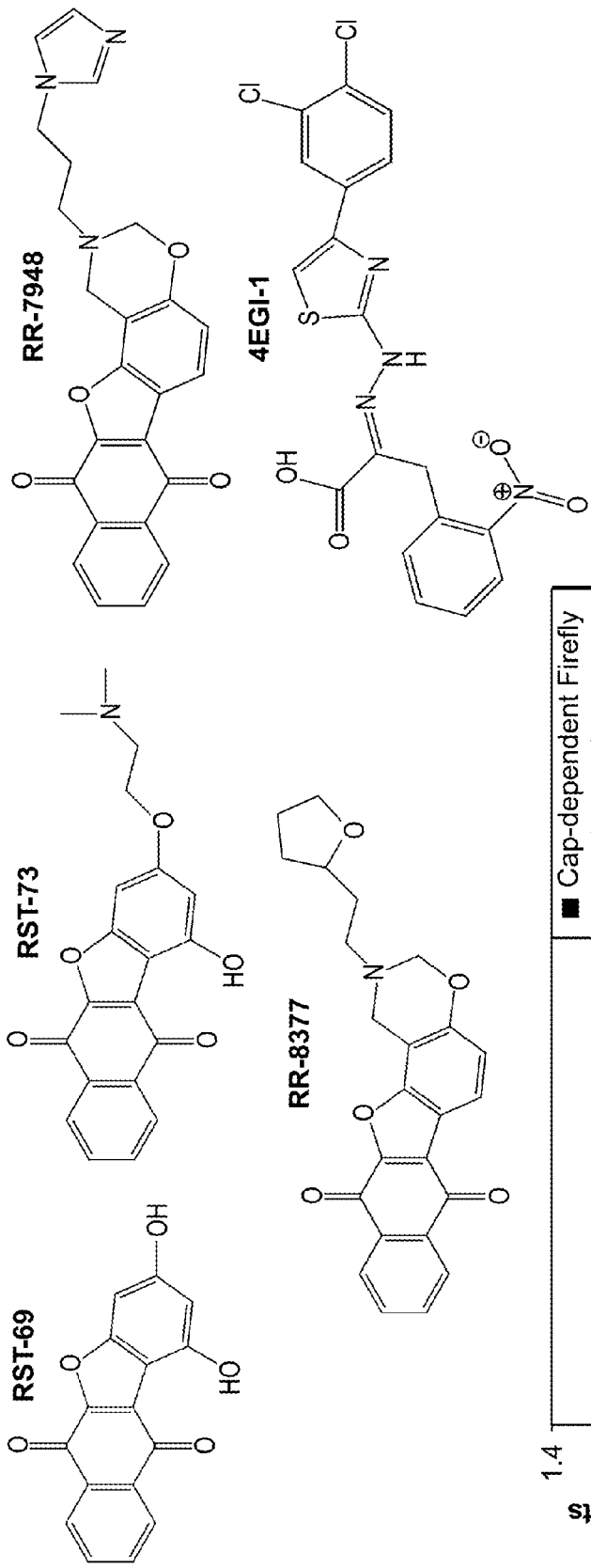
FIG. 5B shows chemical structures of synthesized scaffolds (RST-69, and RST-73) and small molecules (RR-8377, RR-7948, and 4EGI-1) and graphical data of luciferase levels for HeLa cells transfected with a bicistronic luciferase reporter and treated with 5 µM of various compounds for four hours.
Figure 5B:
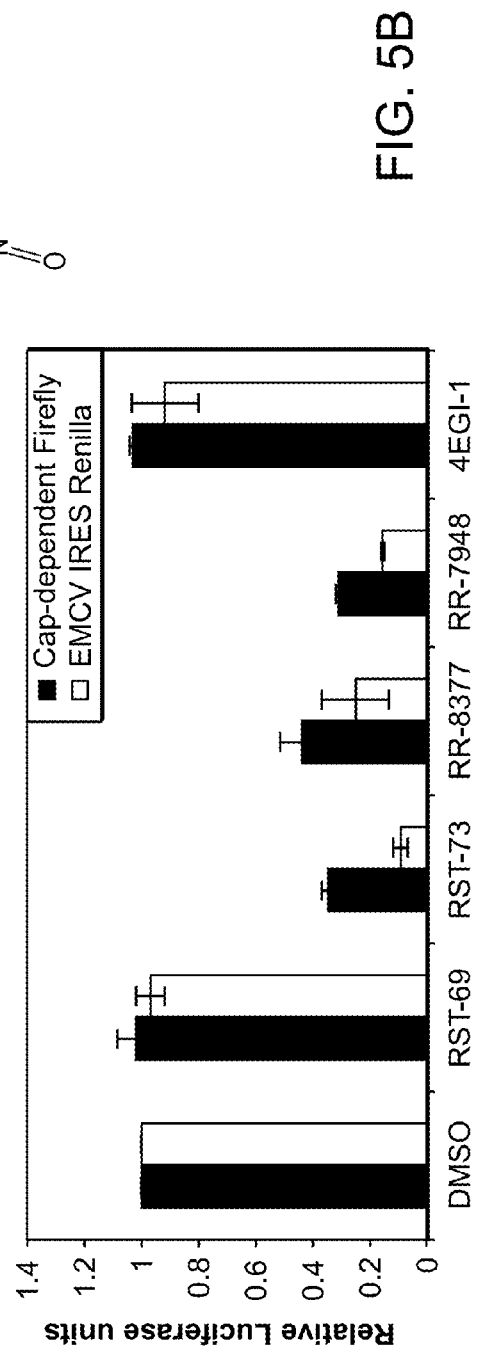
Figure 5C:
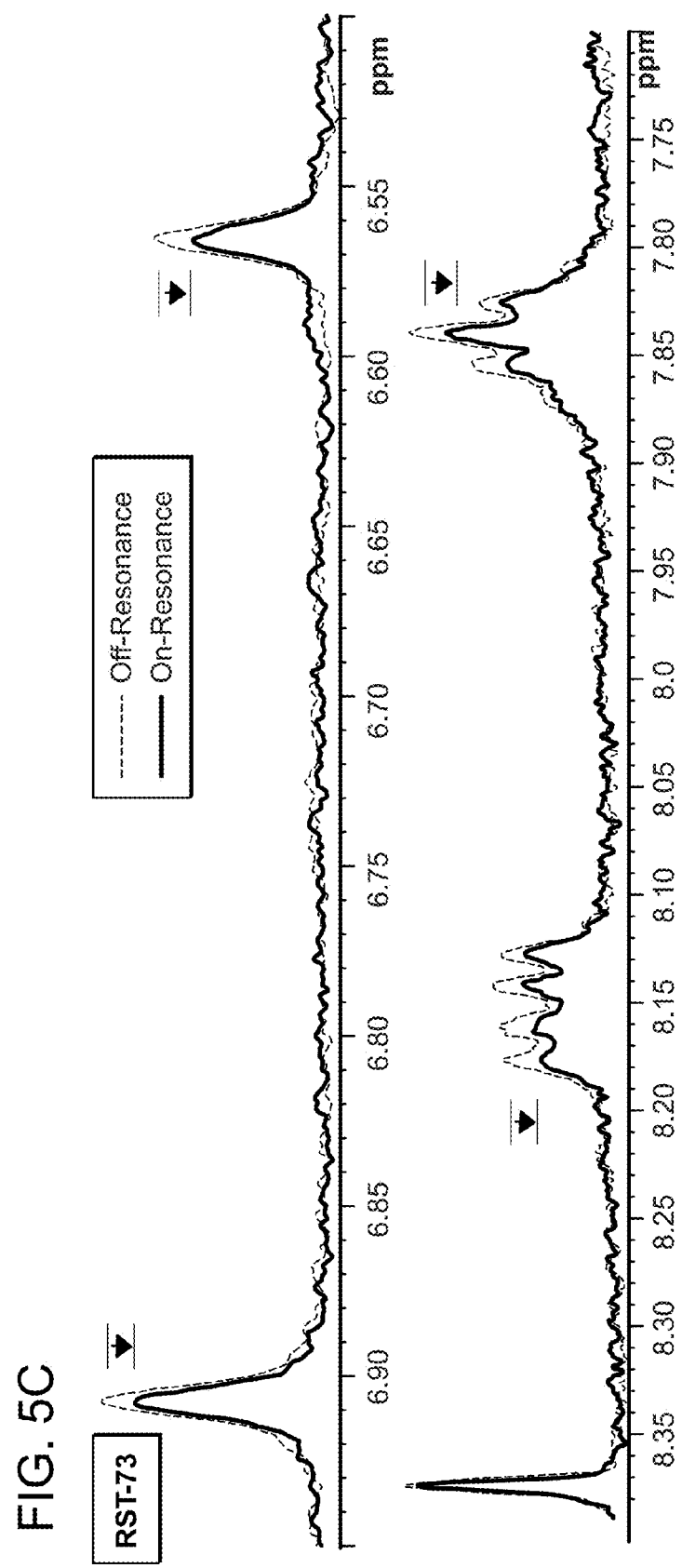
FIG. 5C shows resonances from aromatic protons of RST-73 in the presence of 25 fold excess eIF4E.

FIG. 5: RST-73, representative scaffold for in vivo inhibition of eIF4F complex formation. A) Resonances from aromatic protons of RR-8377 in the presence of 25 fold excess eIF4E. B) Chemical structures of synthesized scaffolds (RST-69, and RST-73) and small molecules (RR-8377, RR-7948, and 4EGI-1). HeLa cells transfected with a bicistronic luciferase reporter were treated with 5 µM of various compounds for four hours and luciferase levels were assessed (Dual Glo, Promega) according to manufacturer's instructions. Values were normalized to signal from DMSO treated cells. C) Resonances from aromatic protons of RST-73 in the presence of 25 fold excess eIF4E.

Figure 6:
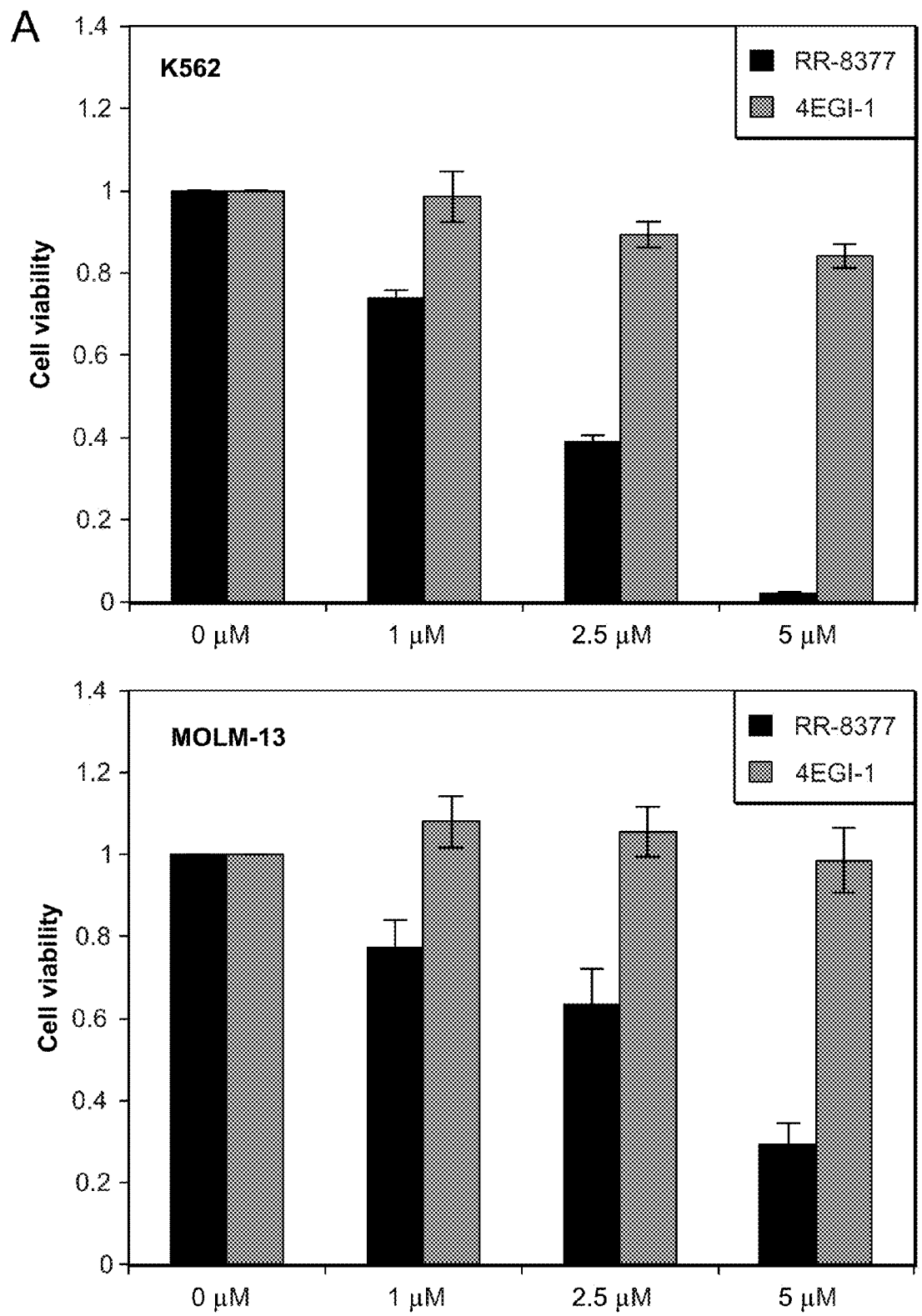
FIG. 6 depicts graphical data of Cell viability of K562, and MOLM-13 cells treated with RR-8377 and 4EGI-1 for twenty-four hours assessed via measuring ATP consumption (Cell Titre Glo, Promega) according to manufacturer's instructions.

FIG. 6: Inhibition of eIF4F complex formation induces apoptosis. A) Cell viability of K562, and MOLM-13 cells treated with RR-8377 and 4EGI-1 for twenty-four hours was assessed via measuring ATP consumption (Cell Titre Glo, Promega) according to manufacturer's instructions.

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application were specifically indicated to be so incorporated by reference.

What is claimed is:

1. A method of inhibiting translation in a human or non-human mammal comprising administering to the human or non-human mammal a compound of Formula

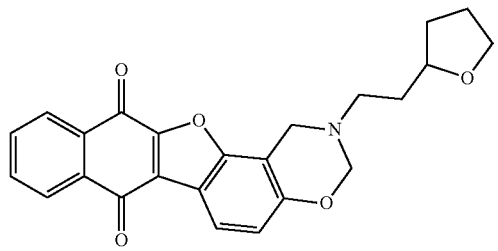 [SMILES: O=C1c2ccccc2C(=O)c2c1oc1c3c(ccc21)OCN(CCC1CCCO1)C3]

or a pharmaceutically acceptable salt thereof.

2. The method of claim 1 wherein the compound is administered by inhalation, transdermally, orally, rectally, transmucosally, intestinally, parenterally, intramuscularly, subcutaneously or intravenously.

3. The method of claim 1, wherein the compound is administered with a therapeutic agent.

* * * * *

UNITED STATES PATENT AND TRADEMARK OFFICE
CERTIFICATE OF CORRECTION

PATENT NO. : 9,956,226 B2
APPLICATION NO. : 14/767102
DATED : May 1, 2018
INVENTOR(S) : Wagner et al.

Page 1 of 1

It is certified that error appears in the above-identified patent and that said Letters Patent is hereby corrected as shown below:

In the Specification

Under STATEMENT OF GOVERNMENT INTERESTS Column 1, Line 14:
Please delete "This invention was made with Government support under grant number NIH P01-GM047467 and R01-CA068262, NIH/NHBLI T32-HL07623-25, NIH K01-DK05198 and NIH R01 AI090671. The government has certain rights in the invention."
And insert --This invention was made with government support under CA068262, GM047467, HL007623, DK005198, and AI090671 awarded by the National Institutes of Health. The government has certain rights in the invention.--

Signed and Sealed this
Ninth Day of June, 2020

Andrei Iancu
*Director of the United States Patent and Trademark Office*